(12) United States Patent
Boisvert et al.

(10) Patent No.: US 7,423,123 B2
(45) Date of Patent: Sep. 9, 2008

(54) INTERLEUKIN-9 ANTAGONIST MUTEINS AND THEIR PHARMACOLOGICAL METHODS OF USE

(75) Inventors: David C. Boisvert, El Cerrito, CA (US); Malinda Longphre, Oakland, CA (US); Sydney Morgan Zaremba, Alameda, CA (US); Armen B. Shanafelt, Carmel, IN (US)

(73) Assignee: Aerovance, Inc., Berkeley, CA (US)

( * ) Notice: Subject to any disclaimer, the term of this patent is extended or adjusted under 35 U.S.C. 154(b) by 541 days.

(21) Appl. No.: 10/845,632

(22) Filed: May 14, 2004

(65) Prior Publication Data

US 2004/0247566 A1 Dec. 9, 2004

Related U.S. Application Data

(60) Provisional application No. 60/470,630, filed on May 14, 2003.

(51) Int. Cl.
| | | |
|---|---|---|
| C07K 14/47 | (2006.01) | |
| C12N 15/24 | (2006.01) | |
| C12N 15/64 | (2006.01) | |
| C12P 21/02 | (2006.01) | |

(52) U.S. Cl. .................. 530/351; 424/85.2; 435/320.1; 435/471; 435/69.52

(58) Field of Classification Search .................. None
See application file for complete search history.

(56) References Cited

U.S. PATENT DOCUMENTS

| 5,734,034 A | 3/1998 | Jayasena et al. ........... 536/23.1 |
| 6,261,559 B1 * | 7/2001 | Levitt et al. ............. 424/139.1 |
| 2002/0146391 A1 | 10/2002 | Levitt et al. ................ 424/85.2 |

OTHER PUBLICATIONS

James A. Wells, Biochemistry, vol. 29, No. 37, Sep. 18, 1990.*
Dong, Qu et al., "IL-9 induces chemokine expression in lung epithelial cells and baseline airway eosinophilia in transgenic mice", *Eur. J. Immunol.* vol. 29, pp. 2130-2139, 1999.
Gounni, A.S., et al, "Interleukin-9 enhances interleukin-5 receptor expression, differentiation, and survival of human eosinophils", *Blood*, vol. 96, No. 6, pp. 2163-2171, 2000.
Gruss, H., et al, "Interleukin 9 Is Expressed by Primary and Cultured Hodgkin and Reed-Sternberg Cells", *Cancer Research*, vol. 52, pp. 1026-1031, 1992.
Kunkel, T.A. et al., "Rapid and Efficient Site-Specific Mutagenesis without Phenotypic Selection", *Methods in Enzymology*, vol. 154, pp. 367-382, 1987.
Lemoli, R.M., "Interleukin-9 Stimulates the Proliferation of Human Myeloid Leukemic Cells", *Blood*, vol. 87, No. 9, pp. 3852-3859, 1996.
Longphre, M. et al., "Allergen-induced IL-9 directly stimulates mucin transcription in respiratory epithelial cells", *The Journal of Clinical Investigation*, vol. 104, No. 10, pp. 1375-1382, 1999.
Postma, D.S., "Genetic Susceptibility to Asthma—Bronchial Hyperresponsiveness Coinherited with a Major Gene for Atopy", *The New England Journal of Medicine*, vol. 333, pp. 894-900, 1995.
Renauld, J. et al., "Interleukin-9 Is a Major Anti-Apoptotic Factor for Thymic Lymphomas", *Blood*, vol. 85, No. 5, pp. 1300-1305, 1995.
Ulbrecht, M. et al., "High serum lgE concentrations: Association with HLA-DR and markers on chromosome 5q31 and chromosome 11q13", *J. Allergy Clin Immunol*, vol. 99, No. 6, pp. 828-836, 1997.
Uyttenhove, C. et al., "Functional and structural characterization of P40, a mouse glycoprotein with T-cell growth factor activity", *Proc. Natl. Acad. Sci.*, vol. 85, pp. 6934-6938, 1988.
Waldmann, T.A., "T-cell receptors for cytokines: TGargets for immunotherapy of leukemia/lymphoma", *Annuals of Oncology*, vol. 11 (Suppl. 1), pp. 101-106, 2000.

* cited by examiner

*Primary Examiner*—Elizabeth C. Kemmerer
*Assistant Examiner*—Fozia M Hamud
(74) *Attorney, Agent, or Firm*—DLA Piper US LLP

(57) ABSTRACT

This invention relates to IL-9 muteins that inhibit the activity of wild-type IL-9, multimers and Fc-fusion constructs of IL-9 proteins, and an efficient method to purify IL-9 proteins produced by eukaryotic cells. Related formulations, dosages and methods of administration thereof for therapeutic purposes are also provided. More particularly, these IL-9 muteins, compositions, and methods provide a treatment option for individuals afflicted with conditions where inhibiting IL-9 mediated immune responses would be beneficial, such as allergy, asthma, chronic obstructive pulmonary disease (emphysema and chronic bronchitis), pulmonary and gastro-intestinal mucus hyperplasia, inflammation, immunological disorders, leukemia, and lymphoma.

12 Claims, 10 Drawing Sheets

*Polynucleotide Sequences*

| SEQ ID No. | Name | Sequence |
|---|---|---|
| 1 | Wild-type hIL-9 | atgcttctggccatggtccttacctctgccctgctcctgtgctccgtggcaggcca ggggtgtccaaccttggcggggatcctggacatcaacttcctcatcaacaagat gcaggaagatccagcttccaagtgccactgcagtgctaatgtgaccagttgtctc tgtttgggcattccctctgacaactgcaccagaccatgcttcagtgagagactgtc tcagatgaccaataccaccatgcaaacaagatacccactgattttcagtcgggtg aaaaaatcagttgaagtactaaagaacaacaagtgtccatattttcctgtgaaca gccatgcaaccaaaccacggcaggcaacgcgctgacatttctgaagagtcttct ggaaattttccagaaagaaaagatgagagggatgagaggcaagata |
| 2 | Wild-type hIL-9 Dimer | atgcttctggccatggtccttacctctgccctgctcctgtgctccgtggcaggcca ggggtgtccaaccttggcggggatcctggacatcaacttcctcatcaacaagat gcaggaagatccagcttccaagtgccactgcagtgctaatgtgaccagttgtctc tgtttgggcattccctctgacaactgcaccagaccatgcttcagtgagagactgtc tcagatgaccaataccaccatgcaaacaagatacccactgattttcagtcgggtg aaaaaatcagttgaagtactaaagaacaacaagtgtccatattttcctgtgaaca gccatgcaaccaaaccacggcaggcaacgcgctgacatttctgaagagtcttct ggaaattttccagaaagaaaagatgagagggatgagaggcaagatacagggg tctccaaccttggcggggatcctggacatcaacttcctcatcaacaagatgcagg aagatccagcttccaagtgccactgcagtgctaatgtgaccagttgtctctgtttg ggcattccctctgacaactgcaccagaccatgcttcagtgagagactgtctcaga tgaccaataccaccatgcaaacaagatacccactgattttcagtcgggtgaaaaa atcagttgaagtactaaagaacaacaagtgtccatattttcctgtgaacagccat gcaaccaaaccacggcaggcaacgcgctgacatttctgaagagtcttctggaa attttccagaaagaaaagatgagagggatgagaggcaagata |
| 3 | K136D Monomer | atgcttctggccatggtccttacctctgccctgctcctgtgctccgtggcaggcca ggggtgtccaaccttggcggggatcctggacatcaacttcctcatcaacaagat gcaggaagatccagcttccaagtgccactgcagtgctaatgtgaccagttgtctc tgtttgggcattccctctgacaactgcaccagaccatgcttcagtgagagactgtc tcagatgaccaataccaccatgcaaacaagatacccactgattttcagtcgggtg aaaaaatcagttgaagtactaaagaacaacaagtgtccatattttcctgtgaaca gccatgcaaccaaaccacggcaggcaacgcgctgacatttctgaagagtcttct ggaaattttccagaaagaagacatgagagggatgagaggcaagatataa |
| 4 | K136D Dimer | atgcttctggccatggtccttacctctgccctgctcctgtgctccgtggcaggcca ggggtgtccaaccttggcggggatcctggacatcaacttcctcatcaacaagat gcaggaagatccagcttccaagtgccactgcagtgctaatgtgaccagttgtctc |

FIG. 1-1

*Polynucleotide Sequences*

| | | |
|---|---|---|
| | | tgtttgggcattccctctgacaactgcaccagaccatgcttcagtgagagactgtc tcagatgaccaataccaccatgcaaacaagatacccactgattttcagtcgggtg aaaaaatcagttgaagtactaaagaacaacaagtgtccatattttcctgtgaaca gccatgcaaccaaaccacggcaggcaacgcgctgacatttctgaagagtcttct ggaaattttcagaaagaagacatgagagggatgagaggcaagatacagggg tctccaaccttggcggggatcctggacatcaacttcctcatcaacaagatgcagg aagatccagcttccaagtgccactgcagtgctaatgtgaccagttgtctctgtttg ggcattccctctgacaactgcaccagaccatgcttcagtgagagactgtctcaga tgaccaataccaccatgcaaacaagatacccactgattttcagtcgggtgaaaaa atcagttgaagtactaaagaacaacaagtgtccatattttcctgtgaacagccat gcaaccaaaccacggcaggcaacgcgctgacatttctgaagagtcttctggaa attttcagaaagaagacatgagagggatgagaggcaagata |
| 5 | K134E Monomer | atgcttctggccatggtccttacctctgccctgctcctgtgctccgtggcaggcca ggggtgtccaaccttggcggggatcctggacatcaacttcctcatcaacaagat gcaggaagatccagcttccaagtgccactgcagtgctaatgtgaccagttgtctc tgtttgggcattccctctgacaactgcaccagaccatgcttcagtgagagactgtc tcagatgaccaataccaccatgcaaacaagatacccactgattttcagtcgggtg aaaaaatcagttgaagtactaaagaacaacaagtgtccatattttcctgtgaaca gccatgcaaccaaaccacggcaggcaacgcgctgacatttctgaagagtcttct ggaaattttccaggaggaaaagatgagagggatgagaggcaagatataa |
| 6 | K134E Dimer | atgcttctggccatggtccttacctctgccctgctcctgtgctccgtggcaggcca ggggtgtccaaccttggcggggatcctggacatcaacttcctcatcaacaagat gcaggaagatccagcttccaagtgccactgcagtgctaatgtgaccagttgtctc tgtttgggcattccctctgacaactgcaccagaccatgcttcagtgagagactgtc tcagatgaccaataccaccatgcaaacaagatacccactgattttcagtcgggtg aaaaaatcagttgaagtactaaagaacaacaagtgtccatattttcctgtgaaca gccatgcaaccaaaccacggcaggcaacgcgctgacatttctgaagagtcttct ggaaattttccaggaggaaaagatgagagggatgagaggcaagatacagggg tctccaaccttggcggggatcctggacatcaacttcctcatcaacaagatgcagg aagatccagcttccaagtgccactgcagtgctaatgtgaccagttgtctctgtttg ggcattccctctgacaactgcaccagaccatgcttcagtgagagactgtctcaga tgaccaataccaccatgcaaacaagatacccactgattttcagtcgggtgaaaaa atcagttgaagtactaaagaacaacaagtgtccatattttcctgtgaacagccat gcaaccaaaccacggcaggcaacgcgctgacatttctgaagagtcttctggaa attttccaggaggaaaagatgagagggatgagaggcaagata |
| 7 | Q133K Monomer | atgcttctggccatggtccttacctctgccctgctcctgtgctccgtggcaggcca ggggtgtccaaccttggcggggatcctggacatcaacttcctcatcaacaagat gcaggaagatccagcttccaagtgccactgcagtgctaatgtgaccagttgtctc tgtttgggcattccctctgacaactgcaccagaccatgcttcagtgagagactgtc tcagatgaccaataccaccatgcaaacaagatacccactgattttcagtcgggtg |

FIG. 1-2

*Polynucleotide Sequences*

| | | |
|---|---|---|
| | | aaaaaatcagttgaagtactaaagaacaacaagtgtccatattttcctgtgaaca gccatgcaaccaaaccacggcaggcaacgcgctgacatttctgaagagtcttct ggaaattttcaagaaagaaaagatgagagggatgagaggcaagatataa |
| 8 | Q133K Dimer | atgcttctggccatggtccttacctctgccctgctcctgtgctccgtggcaggcca ggggtgtccaaccttggcggggatcctggacatcaacttcctcatcaacaagat gcaggaagatccagcttccaagtgccactgcagtgctaatgtgaccagttgtctc tgtttgggcattccctctgacaactgcaccagaccatgcttcagtgagagactgtc tcagatgaccaataccaccatgcaaacaagatacccactgattttcagtcgggtg aaaaaatcagttgaagtactaaagaacaacaagtgtccatattttcctgtgaaca gccatgcaaccaaaccacggcaggcaacgcgctgacatttctgaagagtcttct ggaaattttcaagaaagaaaagatgagagggatgagaggcaagatacagggg tctccaaccttggcggggatcctggacatcaacttcctcatcaacaagatgcagg aagatccagcttccaagtgccactgcagtgctaatgtgaccagttgtctctgtttg ggcattccctctgacaactgcaccagaccatgcttcagtgagagactgtctcaga tgaccaataccaccatgcaaacaagatacccactgattttcagtcgggtgaaaaa atcagttgaagtactaaagaacaacaagtgtccatattttcctgtgaacagccat gcaaccaaaccacggcaggcaacgcgctgacatttctgaagagtcttctggaa attttcaagaaagaaaagatgagagggatgagaggcaagata |
| 9 | Q133K Trimer | atgcttctggccatggtccttacctctgccctgctcctgtgctccgtggcaggcca ggggtgtccaaccttggcggggatcctggacatcaacttcctcatcaacaagat gcaggaagatccagcttccaagtgccactgcagtgctaatgtgaccagttgtctc tgtttgggcattccctctgacaactgcaccagaccatgcttcagtgagagactgtc tcagatgaccaataccaccatgcaaacaagatacccactgattttcagtcgggtg aaaaaatcagttgaagtactaaagaacaacaagtgtccatattttcctgtgaaca gccatgcaaccaaaccacggcaggcaacgcgctgacatttctgaagagtcttct ggaaattttcaagaaagaaaagatgagagggatgagaggcaagatacagggg tctccaaccttggcggggatcctggacatcaacttcctcatcaacaagatgcagg aagatccagcttccaagtgccactgcagtgctaatgtgaccagttgtctctgtttg ggcattccctctgacaactgcaccagaccatgcttcagtgagagactgtctcaga tgaccaataccaccatgcaaacaagatacccactgattttcagtcgggtgaaaaa atcagttgaagtactaaagaacaacaagtgtccatattttcctgtgaacagccat gcaaccaaaccacggcaggcaacgcgctgacatttctgaagagtcttctggaa attttcaagaaagaaaagatgagagggatgagaggcaagatacaggggtctcc aaccttggcggggatcctggacatcaacttcctcatcaacaagatgcaggaaga tccagcttccaagtgccactgcagtgctaatgtgaccagttgtctctgtttgggcat tccctctgacaactgcaccagaccatgcttcagtgagagactgtctcagatgacc aataccaccatgcaaacaagatacccactgattttcagtcgggtgaaaaaatcag ttgaagtactaaagaacaacaagtgtccatattttcctgtgaacagccatgcaac caaaccacggcaggcaacgcgctgacatttctgaagagtcttctggaaattttca agaaagaaaagatgagagggatgagaggcaagata |

FIG. 1-3

*Polynucleotide Sequences*

| 10 | K126E/Q133K Monomer | atgcttctggccatggtccttacctctgccctgctcctgtgctccgtggcaggcca ggggtgtccaaccttggcggggatcctggacatcaacttcctcatcaacaagat gcaggaagatccagcttccaagtgccactgcagtgctaatgtgaccagttgtctc tgtttgggcattccctctgacaactgcaccagaccatgcttcagtgagagactgtc tcagatgaccaataccaccatgcaaacaagatacccactgattttcagtcgggtg aaaaaatcagttgaagtactaaagaacaacaagtgtccatattttcctgtgaaca gccatgcaaccaaaccacggcaggcaacgcgctgacatttctggagagtcttct ggaaattttcaagaaagaaaagatgagagggatgagaggcaagata |
|---|---|---|
| 11 | K126E/Q133K Dimer | Atgcttctggccatggtccttacctctgccctgctcctgtgctccgtggcaggcc aggggtgtccaaccttggcggggatcctggacatcaacttcctcatcaacaaga tgcaggaagatccagcttccaagtgccactgcagtgctaatgtgaccagttgtct ctgtttgggcattccctctgacaactgcaccagaccatgcttcagtgagagactgt ctcagatgaccaataccaccatgcaaacaagatacccactgattttcagtcgggt gaaaaaatcagttgaagtactaaagaacaacaagtgtccatattttcctgtgaac agccatgcaaccaaaccacggcaggcaacgcgctgacatttctggagagtctt ctggaaattttcaagaaagaaaagatgagagggatgagaggcaagatacagg ggtctccaaccttggcggggatcctggacatcaacttcctcatcaacaagatgca ggaagatccagcttccaagtgccactgcagtgctaatgtgaccagttgtctctgtt tgggcattccctctgacaactgcaccagaccatgcttcagtgagagactgtctca gatgaccaataccaccatgcaaacaagatacccactgattttcagtcgggtgaaa aaatcagttgaagtactaaagaacaacaagtgtccatattttcctgtgaacagcc atgcaaccaaaccacggcaggcaacgcgctgacatttctggagagtcttctgga aattttcaagaaagaaaagatgagagggatgagaggcaagata |
| 12 | Fc-K126E/Q133K | atggagacagacacactcctgctatgggtactgctgctctgggttccaggttcca ttggtgagtccaaatcttgtgacaaaaactcacacatgcccaccgtgcccagcacc tgaactcctggggggaccgtcagtcttcctcttccccccaaaacccaaggacac cctcatgatctcccggacccctgaggtcacatgcgtggtggtggacgtgagcca cgaagaccctgaggtcaagttcaactggtacgtggacggcgtggaggtgcata atgccaagacaaagccgcgggaggagcagtacaacagcacgtaccgtgtggt cagcgtcctcaccgtcctgcaccaggactggctgaatggcaaggagtacaagt gcaaggtctccaacaaagccctcccagcccccatcgagaaaaccatctccaaa gccaaagggcagccccgagaaccacaggtgtacaccctgcccccatcccgg gatgagctgaccaagaaccaggtcagcctgacctgcctggtcaaaggcttctat cccagcgacatcgccgtggagtgggagagcaatgggcagccggagaacaac tacaagaccacgcctcccgtgctggactccgacggctccttcttcctctacagca agctcaccgtggacaagagcaggtggcagcaggggaacgtcttctcatgctcc gtgatgcatgaggctctgcacaaccactacacgcagaagagcctctccctgtct ccgggtaaagcggccgcaggccaggggtgtccaaccttggcggggatcctgg acatcaacttcctcatcaacaagatgcaggaagatccagcttccaagtgccactg |

FIG. 1-4

*Polynucleotide Sequences*

| | | |
|---|---|---|
| | | cagtgctaatgtgaccagttgtctctgtttgggcattccctctgacaactgcacca gaccatgcttcagtgagagactgtctcagatgaccaataccaccatgcaaacaa gatacccactgattttcagtcgggtgaaaaaatcagttgaagtactaaagaacaa caagtgtccatattttcctgtgaacagccatgcaaccaaaccacggcaggcaac gcgctgacatttctggagagtcttctggaaattttcaagaaagaaaagatgagag ggatgagaggcaagatatag |
| 13 | K126E/Q133K-Fc | atgcttctggccatggtccttacctctgccctgctcctgtgctccgtggcaggcca ggggtgtccaaccttggcggggatcctggacatcaacttcctcatcaacaagat gcaggaagatccagcttccaagtgccactgcagtgctaatgtgaccagttgtctc tgtttgggcattccctctgacaactgcaccagaccatgcttcagtgagagactgtc tcagatgaccaataccaccatgcaaacaagatacccactgattttcagtcgggtg aaaaaatcagttgaagtactaaagaacaacaagtgtccatattttcctgtgaaca gccatgcaaccaaaccacggcaggcaacgcgctgacatttctggagagtcttct ggaaattttcaagaaagaaaagatgagagggatgagaggcaagatagcggcc gcagagtccaaatcttgtgacaaaactcacacatgcccaccgtgcccagcacct gaactcctggggggaccgtcagtcttcctcttccccccaaaacccaaggacacc ctcatgatctcccggacccctgaggtcacatgcgtggtggtggacgtgagccac gaagaccctgaggtcaagttcaactggtacgtggacggcgtggaggtgcataa tgccaagacaaagccgcgggaggagcagtacaacagcacgtaccgtgtggtc agcgtcctcaccgtcctgcaccaggactggctgaatggcaaggagtacaagtg caaggtctccaacaaagccctcccagcccccatcgagaaaaccatctccaaag ccaaagggcagccccgagagccacaggtgtacaccctgcccccatcccggg atgagctgaccaagaaccaggtcagcctgacctgcctggtcaaaggcttctatc ccagcgacatcgccgtggagtgggagagcaatgggcagccggagaacaact acaagaccacgcctcccgtgctggactccgacggctccttcttcctctacagcaa gctcaccgtggacaagagcaggtggcagcaggggaacgtcttctcatgctccg tgatgcatgaggctctgcacaaccactacacgcagaagagcctctccctgtctc cgggtaaatga |
| 14 | H6TEV-K126E/Q133K Dimer | atgcttctggccatggtccttacctctgccctgctcctgtgctccgtggcaggcca aggccatcatcaccatcaccatgactacgacatccccaccaccgaaaacctgta cttccagggggtgtccaaccttggcggggatcctggacatcaacttcctcatcaac aagatgcaggaagatccagcttccaagtgccactgcagtgctaatgtgaccagt tgtctctgtttgggcattccctctgacaactgcaccagaccatgcttcagtgagag actgtctcagatgaccaataccaccatgcaaacaagatacccactgattttcagtc gggtgaaaaaatcagttgaagtactaaagaacaacaagtgtccatattttcctgt gaacagccatgcaaccaaaccacggcaggcaacgcgctgacatttctggaga gtcttctggaaattttcaagaaagaaaagatgagagggatgagaggcaagatac aggggtctccaaccttggcggggatcctggacatcaacttcctcatcaacaagat gcaggaagatccagcttccaagtgccactgcagtgctaatgtgaccagttgtctc tgtttgggcattccctctgacaactgcaccagaccatgcttcagtgagagactgtc tcagatgaccaataccaccatgcaaacaagatacccactgattttcagtcgggtg aaaaaatcagttgaagtactaaagaacaacaagtgtccatattttcctgtgaaca |

FIG. 1-5

*Polynucleotide Sequences*

|  |  | gccatgcaaccaaaccacggcaggcaacgcgctgacatttctggagagtcttct ggaaattttcaagaaagaaaagatgagagggatgagaggcaagata |
|---|---|---|

FIG. 1-6

*Polypeptide Sequences*

| SEQ ID No. | Name | Sequence |
|---|---|---|
| 15 | Wild-type hIL-9 | mllamvltsalllcsvagqgcptlagildinflinkmqedpaskchcsanvtsclclgipsdnctrpcfserlsqmtnttmqtryplifsrvkksvevlknnkcpyfsceqpcnqttagnaltflkslleifqkekmrgmrgki |
| 16 | Wild-type hIL-9 Dimer | mllamvltsalllcsvagqgcptlagildinflinkmqedpaskchcsanvtsclclgipsdnctrpcfserlsqmtnttmqtryplifsrvkksvevlknnkcpyfsceqpcnqttagnaltflkslleifqkekmrgmrgkiqgsptlagildinflinkmqedpaskchcsanvtsclclgipsdnctrpcfserlsqmtnttmqtryplifsrvkksvevlknnkcpyfsceqpcnqttagnaltflkslleifqkekmrgmrgki |
| 17 | K136D Monomer | mllamvltsalllcsvagqgcptlagildinflinkmqedpaskchcsanvtsclclgipsdnctrpcfserlsqmtnttmqtryplifsrvkksvevlknnkcpyfsceqpcnqttagnaltflkslleifqkedmrgmrgki |
| 18 | K136D Dimer | mllamvltsalllcsvagqgcptlagildinflinkmqedpaskchcsanvtsclclgipsdnctrpcfserlsqmtnttmqtryplifsrvkksvevlknnkcpyfsceqpcnqttagnaltflkslleifqkedmrgmrgkiqgsptlagildinflinkmqedpaskchcsanvtsclclgipsdnctrpcfserlsqmtnttmqtryplifsrvkksvevlknnkcpyfsceqpcnqttagnaltflkslleifqkedmrgmrgki |
| 19 | K134E Monomer | mllamvltsalllcsvagqgcptlagildinflinkmqedpaskchcsanvtsclclgipsdnctrpcfserlsqmtnttmqtryplifsrvkksvevlknnkcpyfsceqpcnqttagnaltflkslleifqeekmrgmrgki |

FIG. 2-1

*Polypeptide Sequences*

| 20 | K134E Dimer | mllamvltsalllcsvagqgcptlagildinflinkmqedpaskchcsanvtsclclgipsdnctrpcfserlsqmtnttmqtryplifsrvkksvevlknnkcpyfsceqpcnqttagnaltflkslleifqeekmrgmrgkiqgsptlagildinflinkmqedpaskchcsanvtsclclgipsdnctrpcfserlsqmtnttmqtryplifsrvkksvevlknnkcpyfsceqpcnqttagnaltflkslleifqeekmrgmrgki |
| --- | --- | --- |
| 21 | Q133K Monomer | mllamvltsalllcsvagqgcptlagildinflinkmqedpaskchcsanvtsclclgipsdnctrpcfserlsqmtnttmqtryplifsrvkksvevlknnkcpyfsceqpcnqttagnaltflkslleifkkekmrgmrgki |
| 22 | Q133K Dimer | mllamvltsalllcsvagqgcptlagildinflinkmqedpaskchcsanvtsclclgipsdnctrpcfserlsqmtnttmqtryplifsrvkksvevlknnkcpyfsceqpcnqttagnaltflkslleifkkekmrgmrgkiqgsptlagildinflinkmqedpaskchcsanvtsclclgipsdnctrpcfserlsqmtnttmqtryplifsrvkksvevlknnkcpyfsceqpcnqttagnaltflkslleifkkekmrgmrgki |
| 23 | Q133K Trimer | mllamvltsalllcsvagqgcptlagildinflinkmqedpaskchcsanvtsclclgipsdnctrpcfserlsqmtnttmqtryplifsrvkksvevlknnkcpyfsceqpcnqttagnaltflkslleifkkekmrgmrgkiqgsptlagildinflinkmqedpaskchcsanvtsclclgipsdnctrpcfserlsqmtnttmqtryplifsrvkksvevlknnkcpyfsceqpcnqttagnaltflkslleifkkekmrgmrgkiqgsptlagildinflinkmqedpaskchcsanvtsclclgipsdnctrpcfserlsqmtnttmqtryplifsrvkksvevlknnkcpyfsceqpcnqttagnaltflkslleifkkekmrgmrgki |
| 24 | K126E/Q133K Monomer | mllamvltsalllcsvagqgcptlagildinflinkmqedpaskchcsanvtsclclgipsdnctrpcfserlsqmtnttmqtryplifsrvkksvevlknnkcpyfsceqpcnqttagnaltfleslleifkkekmrgmrgki |
| 25 | K126E/Q133K Dimer | mllamvltsalllcsvagqgcptlagildinflinkmqedpaskchcsanvtsclclgipsdnctrpcfserlsqmtnttmqtryplifsrvkksvevlknnkcpyfsceqpcnqttagnaltfleslleifkkekmrgmrgkiqgsptlagildinflinkmqedpaskchcsanvtsclclgipsdnctrpcfserlsqmtnttmqtryplifsrvkksvevlknnkcpyfsceqpcnqttagnaltfleslleifkkekmrgmrgki |
| 26 | Fc-K126E/Q133K | metdtlllwvlllwvpgsigcskscdkthtcppcpapellggpsvflfppkpkdtlmisrtpevtcvvvdvshedpevkfnwyvdgvevhnaktkpreeqynstyrvvsvltvlhqdwlngkeykckvsnkalpapiektiskakgqprepqvytlppsrdeltknqvsltclvkgfypsdiavewesngqpennykttp |

FIG. 2-2

*Polypeptide Sequences*

| | | |
|---|---|---|
| | | pvldsdgsfflyskltvdksrwqqgnvfscsvmhealhnhytqkslslsp gkaaagqgcptlagildinflinkmqedpaskchcsanvtsclclgipsdn ctrpcfserlsqmtnttmqtryplifsrvkksvevlknnkcpyfsceqpcn qttagnaltfleslleifkkekmrgmrgki |
| 27 | K126E/Q133K-Fc | mllamvltsalllcsvagqgcptlagildinflinkmqedpaskchcsanvt sclclgipsdnctrpcfserlsqmtnttmqtryplifsrvkksvevlknnkcp yfsceqpcnqttagnaltfleslleifkkekmrgmrgkiaaaeskscdktht cppcpapellggpsvflfppkpkdtlmisrtpevtcvvvdvshedpevkf nwyvdgvevhnaktkpreeqynstyrvvsvltvlhqdwlngkeykckv snkalpapiektiskakgqprepqvytlppsrdeltknqvsltclvkgfyps diavewesngqpennykttppvldsdgsfflyskltvdksrwqqgnvfsc svmhealhnhytqkslslspgk |
| 28 | Uncleaved TEV K126E/Q133K Dimer | mllamvltsalllcsvagqghhhhhhdydipttenlyfqgcptlagildinfl inkmqedpaskchcsanvtsclclgipsdnctrpcfserlsqmtnttmqtr yplifsrvkksvevlknnkcpyfsceqpcnqttagnaltfleslleifkkek mrgmrgkiqgsptlagildinflinkmqedpaskchcsanvtsclclgips dnctrpcfserlsqmtnttmqtryplifsrvkksvevlknnkcpyfsceqp cnqttagnaltfleslleifkkekmrgmrgki |
| 29 | Cleaved TEV K126E/Q133K Dimer | gcptlagildinflinkmqedpaskchcsanvtsclclgipsdnctrpcfser lsqmtnttmqtryplifsrvkksvevlknnkcpyfsceqpcnqttagnaltf leslleifkkekmrgmrgkiqgsptlagildinflinkmqedpaskchcsa nvtsclclgipsdnctrpcfserlsqmtnttmqtryplifsrvkksvevlknn kcpyfsceqpcnqttagnaltfleslleifkkekmrgmrgki |

FIG. 2-3

Mo7E Proliferation Assay Results

| Name | SEQ ID No. | EC50 (nM) |
|---|---|---|
| Wild-type hIL-9 Monomer | 14 | 0.04 |
| Wild-type hIL-9 Dimer | 15 | 0.04 |

FIG. 3

Mo7E Proliferation Assay Results

| Name | SEQ ID No. | IC50 (nM) |
|---|---|---|
| K136D Monomer | 17 | 403.80 |
| K134E Monomer | 19 | 186.10 |
| Q133K Monomer | 21 | 14.70 |
| Q133K Trimer | 23 | 12.05 |
| K126E/Q133K Monomer | 24 | 4.16 |
| K126E/Q133K Dimer | 25 | 3.51 |
| Fc-K126E/Q133K | 26 | 1.15 |
| K126E/Q133K-Fc | 27 | 0.66 |
| Uncleaved H6TEV-K126E/Q133K Dimer | 28 | 11.07 |
| Cleaved H6TEV-K126E/Q133K Dimer | 29 | 8.06 |

FIG. 4

Human & Cynomolgus Monkey Eosinophil Survival Assay Results

| Name | SEQ ID No. | Species | IC50 (nM) |
| --- | --- | --- | --- |
| K136D Monomer | 17 | Human | 74.09 |
| K136D Dimer | 18 | Human | 2.85 |
| K134E Monomer | 19 | Human | 121.70 |
| K134E Dimer | 20 | Human | 91.28 |
| Q133K Monomer | 21 | Human | 63.38 |
| Q133K Dimer | 22 | Human | 177.44 |
| Q133K Trimer | 23 | Human | 102.30 |
| K126E/Q133K Monomer | 24 | Human | 32.50 |
| K126E/Q133K Monomer | 24 | Cynomolgus Monkey | 41.05 |
| K126E/Q133K Dimer | 25 | Human | 12.31 |
| Fc-K126E/Q133K | 26 | Human | 25.48 |
| K126E/Q133K-Fc | 27 | Human | 4.92 |

FIG. 5

SEQUENCE LISTING

```
<160> NUMBER OF SEQ ID NOS: 29

<210> SEQ ID NO 1
<211> LENGTH: 492
<212> TYPE: DNA
<213> ORGANISM: Wild-type hIL-9

<400> SEQUENCE: 1
atgcttctgg ccatggtcct tacctctgcc ctgctcctgt gctccgtggc aggccagggg     60
atgcttctgg ccatggtcct tacctctgcc ctgctcctgt gctccgtggc aggccagggg    120
tgtccaacct tggcggggat cctggacatc aacttcctca tcaacaagat gcaggaagat    180
ccagcttcca agtgccactg cagtgctaat gtgaccagtt gtctctgttt gggcattccc    240
tctgacaact gcaccagacc atgcttcagt gagagactgt ctcagatgac caataccacc    300
atgcaaacaa gatacccact gattttcagt cgggtgaaaa aatcagttga agtactaaag    360
aacaacaagt gtccatattt ttcctgtgaa cagccatgca accaaaccac ggcaggcaac    420
gcgctgacat ttctgaagag tcttctggaa attttccaga aagaaaagat gagagggatg    480
agaggcaaga ta                                                        492

<210> SEQ ID NO 2
<211> LENGTH: 810
<212> TYPE: DNA
<213> ORGANISM: Wild-type hIL-9 Dimer

<400> SEQUENCE: 2
atgcttctgg ccatggtcct tacctctgcc ctgctcctgt gctccgtggc aggccagggg     60
tgtccaacct tggcggggat cctggacatc aacttcctca tcaacaagat gcaggaagat    120
ccagcttcca agtgccactg cagtgctaat gtgaccagtt gtctctgttt gggcattccc    180
tctgacaact gcaccagacc atgcttcagt gagagactgt ctcagatgac caataccacc    240
atgcaaacaa gatacccact gattttcagt cgggtgaaaa aatcagttga agtactaaag    300
aacaacaagt gtccatattt ttcctgtgaa cagccatgca accaaaccac ggcaggcaac    360
gcgctgacat ttctgaagag tcttctggaa attttccaga aagaaaagat gagagggatg    420
agaggcaaga tacaggggtc tccaaccttg gcggggatcc tggacatcaa cttcctcatc    480
aacaagatgc aggaagatcc agcttccaag tgccactgca gtgctaatgt gaccagttgt    540
ctctgtttgg gcattccctc tgacaactgc accagaccat gcttcagtga gagactgtct    600
```

```
cagatgacca ataccaccat gcaaacaaga tacccactga ttttcagtcg ggtgaaaaaa      660
tcagttgaag tactaaagaa caacaagtgt ccatattttt cctgtgaaca gccatgcaac      720
caaaccacgg caggcaacgc gctgacattt ctgaagagtc ttctggaaat tttccagaaa      780
gaaaagatga gagggatgag aggcaagata                                       810
```

<210> SEQ ID NO 3
<211> LENGTH: 435
<212> TYPE: DNA
<213> ORGANISM: K136D Monomer

<400> SEQUENCE: 3

```
atgcttctgg ccatggtcct tacctctgcc ctgctcctgt gctccgtggc aggccagggg       60
tgtccaacct tggcggggat cctggacatc aacttcctca tcaacaagat gcaggaagat      120
ccagcttcca agtgccactg cagtgctaat gtgaccagtt gtctctgttt gggcattccc      180
tctgacaact gcaccagacc atgcttcagt gagagactgc tcagatgacc aataccacc      240 atgcaaacaa gatacccact gattttcagt cgggtgaaaa aatcagttga agtactaaag      300
aacaacaagt gtccatattt ttcctgtgaa cagccatgca accaaaccac ggcaggcaac      360
gcgctgacat ttctgaagag tcttctggaa attttccaga agaagacat gagagggatg       420 agaggcaaga tataa                                                       435
```

<210> SEQ ID NO 4
<211> LENGTH: 810
<212> TYPE: DNA
<213> ORGANISM: K136D Dimer

<400> SEQUENCE: 4

```
atgcttctgg ccatggtcct tacctctgcc ctgctcctgt gctccgtggc aggccagggg       60
tgtccaacct tggcggggat cctggacatc aacttcctca tcaacaagat gcaggaagat      120
ccagcttcca agtgccactg cagtgctaat gtgaccagtt gtctctgttt gggcattccc      180
tctgacaact gcaccagacc atgcttcagt gagagactgt ctcagatgac caataccacc      240
atgcaaacaa gatacccact gattttcagt cgggtgaaaa aatcagttga agtactaaag      300
aacaacaagt gtccatattt ttcctgtgaa cagccatgca accaaaccac ggcaggcaac      360
gcgctgacat ttctgaagag tcttctggaa attttccaga agaagacat gagagggatg       420 agaggcaaga tacaggggtc tccaaccttg gcggggatcc tggacatcaa cttcctcatc      480
aacaagatgc aggaagatcc agcttccaag tgccactgca gtgctaatgt gaccagttgt      540
ctctgtttgg gcattccctc tgacaactgc accagaccat gcttcagtga gagactgtct      600
cagatgacca ataccaccat gcaaacaaga tacccactga ttttcagtcg ggtgaaaaaa      660
tcagttgaag tactaaagaa caacaagtgt ccatattttt cctgtgaaca gccatgcaac      720
caaaccacgg caggcaacgc gctgacattt ctgaagagtc ttctggaaat tttccagaaa      780
gaagacatga gagggatgag aggcaagata                                       810
```

<210> SEQ ID NO 5
<211> LENGTH: 435
<212> TYPE: DNA
<213> ORGANISM: K134E Monomer

<400> SEQUENCE: 5

```
atgcttctgg ccatggtcct tacctctgcc ctgctcctgt gctccgtggc aggccagggg       60
tgtccaacct tggcggggat cctggacatc aacttcctca tcaacaagat gcaggaagat      120
```

-continued

```
ccagcttcca agtgccactg cagtgctaat gtgaccagtt gtctctgttt gggcattccc      180
tctgacaact gcaccagacc atgcttcagt gagagactgt ctcagatgac caataccacc      240
atgcaaacaa gatcccact gattttcagt cgggtgaaaa aatcagttga agtactaaag       300
aacaacaagt gtccatattt ttcctgtgaa cagccatgca accaaaccac ggcaggcaac      360
gcgctgacat ttctgaagag tcttctggaa attttccagg aggaaaagat gagagggatg      420
agaggcaaga tataa                                                       435

<210> SEQ ID NO 6
<211> LENGTH: 810
<212> TYPE: DNA
<213> ORGANISM: K134E Dimer

<400> SEQUENCE: 6
atgcttctgg ccatggtcct tacctctgcc ctgctcctgt gctccgtggc aggccagggg       60
tgtccaacct tggcggggat cctggacatc aacttcctca tcaacaagat gcaggaagat      120
ccagcttcca agtgccactg cagtgctaat gtgaccagtt gtctctgttt gggcattccc      180
tctgacaact gcaccagacc atgcttcagt gagagactgt ctcagatgac caataccacc      240
atgcaaacaa gatcccact gattttcagt cgggtgaaaa aatcagttga agtactaaag       300
aacaacaagt gtccatattt ttcctgtgaa cagccatgca accaaaccac ggcaggcaac      360
gcgctgacat ttctgaagag tcttctggaa attttccagg aggaaaagat gagagggatg      420
agaggcaaga tacaggggtc tccaaccttg gcggggatcc tggacatcaa cttcctcatc      480
aacaagatgc aggaagatcc agcttccaag tgccactgca gtgctaatgt gaccagttgt      540
ctctgtttgg gcattccctc tgacaactgc accagaccat gcttcagtga gagactgtct      600
cagatgacca ataccaccat gcaaacaaga tacccactga ttttcagtcg ggtgaaaaaa      660
tcagttgaag tactaaagaa caacaagtgt ccatattttt cctgtgaaca gccatgcaac      720
caaaccacgg caggcaacgc gctgacattt ctgaagagtc ttctggaaat tttccaggag      780
gaaaagatga gagggatgag aggcaagata                                       810

<210> SEQ ID NO 7
<211> LENGTH: 435
<212> TYPE: DNA
<213> ORGANISM: Q133K Monomer

<400> SEQUENCE: 7
atgcttctgg ccatggtcct tacctctgcc ctgctcctgt gctccgtggc aggccagggg       60
tgtccaacct tggcggggat cctggacatc aacttcctca tcaacaagat gcaggaagat      120
ccagcttcca agtgccactg cagtgctaat gtgaccagtt gtctctgttt gggcattccc      180
tctgacaact gcaccagacc atgcttcagt gagagactgt ctcagatgac caataccacc      240
atgcaaacaa gatcccact gattttcagt cgggtgaaaa aatcagttga agtactaaag       300
aacaacaagt gtccatattt ttcctgtgaa cagccatgca accaaaccac ggcaggcaac      360
gcgctgacat ttctgaagag tcttctggaa attttcaaga agaaaagat gagagggatg      420 agaggcaaga tataa                                                       435

<210> SEQ ID NO 8
<211> LENGTH: 810
<212> TYPE: DNA
<213> ORGANISM: Q133K Dimer
```

<400> SEQUENCE: 8

```
atgcttctgg ccatggtcct tacctctgcc ctgctcctgt gctccgtggc aggccagggg      60
tgtccaacct tggcggggat cctggacatc aacttcctca tcaacaagat gcaggaagat     120
ccagcttcca gtgccactg cagtgctaat gtgaccagtt gtctctgttt gggcattccc     180
tctgacaact gcaccagacc atgcttcagt gagagactgt ctcagatgac caataccacc    240
atgcaaacaa gatacccact gattttcagt cgggtgaaaa aatcagttga agtactaaag    300
aacaacaagt gtccatattt ttcctgtgaa cagccatgca accaaaccac ggcaggcaac    360
gcgctgacat ttctgaagag tcttctggaa attttcaaga agaaaagat gagagggatg     420
agaggcaaga tacaggggtc tccaaccttg gcggggatcc tggacatcaa cttcctcatc    480
aacaagatgc aggaagatcc agcttccaag tgccactgca gtgctaatgt gaccagttgt    540
ctctgtttgg gcattccctc tgacaactgc accagaccat gcttcagtga gagactgtct    600
cagatgacca ataccaccat gcaaacaaga tacccactga ttttcagtcg ggtgaaaaaa    660
tcagttgaag tactaaagaa caacaagtgt ccatattttt cctgtgaaca gccatgcaac    720
caaaccacgg caggcaacgc gctgacattt ctgaagagtc ttctggaaat tttcaagaaa    780
gaaaagatga gagggatgag aggcaagata                                     810
```

<210> SEQ ID NO 9
<211> LENGTH: 1188
<212> TYPE: DNA
<213> ORGANISM: Q133K Trimer

<400> SEQUENCE: 9

```
atgcttctgg ccatggtcct tacctctgcc ctgctcctgt gctccgtggc aggccagggg      60
tgtccaacct tggcggggat cctggacatc aacttcctca tcaacaagat gcaggaagat     120
ccagcttcca gtgccactg cagtgctaat gtgaccagtt gtctctgttt gggcattccc     180
tctgacaact gcaccagacc atgcttcagt gagagactgt ctcagatgac caataccacc    240
atgcaaacaa gatacccact gattttcagt cgggtgaaaa aatcagttga agtactaaag    300
aacaacaagt gtccatattt ttcctgtgaa cagccatgca accaaaccac ggcaggcaac    360
gcgctgacat ttctgaagag tcttctggaa attttcaaga agaaaagat gagagggatg     420
agaggcaaga tacaggggtc tccaaccttg gcggggatcc tggacatcaa cttcctcatc    480
aacaagatgc aggaagatcc agcttccaag tgccactgca gtgctaatgt gaccagttgt    540
ctctgtttgg gcattccctc tgacaactgc accagaccat gcttcagtga gagactgtct    600
cagatgacca ataccaccat gcaaacaaga tacccactga ttttcagtcg ggtgaaaaaa    660
tcagttgaag tactaaagaa caacaagtgt ccatattttt cctgtgaaca gccatgcaac    720
caaaccacgg caggcaacgc gctgacattt ctgaagagtc ttctggaaat tttcaagaaa    780
gaaaagatga gagggatgag aggcaagata cagggggtctc caaccttggc ggggatcctg    840
gacatcaact tcctcatcaa caagatgcag gaagatccag cttccaagtg ccactgcagt    900
gctaatgtga ccagttgtct ctgtttggc attccctctg acaactgcac cagaccatgc     960
ttcagtgaga ctgtctca gatgaccaat accaccatgc aaacaagata cccactgatt    1020
ttcagtcggg tgaaaaaatc agttgaagta ctaaagaaca acaagtgtcc atatttttcc   1080
tgtgaacagc catgcaacca aaccacggca ggcaacgcgc tgacatttct gaagagtctt   1140
ctggaaattt tcaagaaaga aaagatgaga gggatgagag gcaagata                 1188
```

<210> SEQ ID NO 10
<211> LENGTH: 432
<212> TYPE: DNA
<213> ORGANISM: K126E/Q133K Monomer

<400> SEQUENCE: 10

| | | | | | |
|---|---|---|---|---|---|
| atgcttctgg | ccatggtcct | tacctctgcc | ctgctcctgt | gctccgtggc | aggccagggg | 60 |
| tgtccaacct | tggcggggat | cctggacatc | aacttcctca | tcaacaagat | gcaggaagat | 120 |
| ccagcttcca | agtgccactg | cagtgctaat | gtgaccagtt | gtctctgttt | gggcattccc | 180 |
| tctgacaact | gcaccagacc | atgcttcagt | gagagactgt | ctcagatgac | caataccacc | 240 |
| atgcaaacaa | gatacccact | gattttcagt | cgggtgaaaa | atcagttga | agtactaaag | 300 |
| aacaacaagt | gtccatattt | tcctgtgaa | cagccatgca | accaaaccac | ggcaggcaac | 360 |
| gcgctgacat | ttctggagag | tcttctgaa | attttcaaga | agaaaagat | gagagggatg | 420 |
| agaggcaaga | ta | | | | | 432 |

<210> SEQ ID NO 11
<211> LENGTH: 810
<212> TYPE: DNA
<213> ORGANISM: K126E/Q133K Dimer

<400> SEQUENCE: 11

| | | | | | |
|---|---|---|---|---|---|
| atgcttctgg | ccatggtcct | tacctctgcc | ctgctcctgt | gctccgtggc | aggccagggg | 60 |
| tgtccaacct | tggcggggat | cctggacatc | aacttcctca | tcaacaagat | gcaggaagat | 120 |
| ccagcttcca | agtgccactg | cagtgctaat | gtgaccagtt | gtctctgttt | gggcattccc | 180 |
| tctgacaact | gcaccagacc | atgcttcagt | gagagactgt | ctcagatgac | caataccacc | 240 |
| atgcaaacaa | gatacccact | gattttcagt | cgggtgaaaa | atcagttga | agtactaaag | 300 |
| aacaacaagt | gtccatattt | tcctgtgaa | cagccatgca | accaaaccac | ggcaggcaac | 360 |
| gcgctgacat | ttctggagag | tcttctgaa | attttcaaga | agaaaagat | gagagggatg | 420 |
| agaggcaaga | tacaggggtc | tccaaccttg | gcggggatcc | tggacatcaa | cttcctcatc | 480 |
| aacaagatgc | aggaagatcc | agcttccaag | tgccactgca | gtgctaatgt | gaccagttgt | 540 |
| ctctgtttgg | gcattccctc | tgacaactgc | accagaccat | gcttcagtga | gagactgtct | 600 |
| cagatgacca | ataccaccat | gcaaacaaga | tacccactga | ttttcagtcg | ggtgaaaaaa | 660 |
| tcagttgaag | tactaaagaa | caacaagtgt | ccatattttt | cctgtgaaca | gccatgcaac | 720 |
| caaaccacgg | caggcaacgc | gctgacattt | ctggagagtc | ttctggaaat | tttcaagaaa | 780 |
| gaaaagatga | gagggatgag | aggcaagata | | | | 810 |

<210> SEQ ID NO 12
<211> LENGTH: 1149
<212> TYPE: DNA
<213> ORGANISM: Fc-K126E/Q133K

<400> SEQUENCE: 12

| | | | | | |
|---|---|---|---|---|---|
| atggagacag | acacactcct | gctatgggta | ctgctgctct | gggttccagg | ttccattggt | 60 |
| gagtccaaat | cttgtgacaa | aactcacaca | tgcccaccgt | gcccagcacc | tgaactcctg | 120 |
| gggggaccgt | cagtcttcct | cttccccca | aaacccaagg | acaccctcat | gatctcccgg | 180 |
| accccctgagg | tcacatgcgt | ggtggtggac | gtgagccacg | aagaccctga | ggtcaagttc | 240 |
| aactggtacg | tggacggcgt | ggaggtgcat | aatgccaaga | caaagccgcg | ggaggagcag | 300 |
| tacaacagca | cgtaccgtgt | ggtcagcgtc | ctcaccgtcc | tgcaccagga | ctggctgaat | 360 |

```
ggcaaggagt acaagtgcaa ggtctccaac aaagccctcc cagcccccat cgagaaaacc      420
atctccaaag ccaagggca gccccgagaa ccacaggtgt acaccctgcc cccatcccgg       480
gatgagctga ccaagaacca ggtcagcctg acctgcctgg tcaaaggctt ctatcccagc      540
gacatcgccg tggagtggga gagcaatggg cagccggaga caactacaa gaccacgcct      600 cccgtgctgg actccgacgg ctccttcttc ctctacagca agctcaccgt ggacaagagc     660
aggtggcagc aggggaacgt cttctcatgc tccgtgatgc atgaggctct gcacaaccac    720
tacacgcaga gagcctctc cctgtctccg ggtaaagcgg ccgcaggcca ggggtgtcca     780
accttggcgg ggatcctgga catcaacttc ctcatcaaca gatgcagga gatccagct     840 tccaagtgcc actgcagtgc taatgtgacc agttgtctct gtttgggcat ccctctgac    900 aactgcacca ccatgcttc cagtgagaga ctgtctcaga tgaccaatac caccatgcaa    960
acaagatacc cactgatttt cagtcgggtg aaaaaatcag ttgaagtact aaagaacaac   1020
aagtgtccat attttcctg tgaacagcca tgcaaccaaa ccacggcagg caacgcgctg    1080
acatttctgg agagtcttct ggaaattttc aagaaagaaa agatgagagg gatgagaggc   1140
aagatatag                                                            1149
```

<210> SEQ ID NO 13
<211> LENGTH: 1140
<212> TYPE: DNA
<213> ORGANISM: K126E/Q133K-Fc

<400> SEQUENCE: 13

```
atgcttctgg ccatggtcct tacctctgcc ctgctcctgt gctccgtggc aggccagggg     60
tgtccaacct tggcggggat cctggacatc aacttcctca tcaacaagat gcaggaagat    120
ccagcttcca gtgccactg cagtgctaat gtgaccagtt gtctctgttt gggcattccc     180
tctgacaact gcaccagacc atgcttcagt gagagactgt ctcagatgac caataccacc    240
atgcaaacaa gataccccact gattttcagt cgggtgaaaa aatcagttga agtactaaag    300
aacaacaagt gtccatattt ttcctgtgaa cagccatgca accaaaccac ggcaggcaac    360
gcgctgacat ttctggagag tcttctggaa attttcaaga agaaaagat gagagggatg     420 agaggcaaga tagcggccgc agagtccaaa tcttgtgaca aaactcacac atgcccaccg   480
tgcccagcac ctgaactcct ggggggaccg tcagtcttcc tcttcccccc aaaacccaag   540
gacaccctca tgatctcccg gacccctgag gtcacatgcg tggtggtgga cgtgagccac   600
gaagaccctg aggtcaagtt caactggtac gtggacggcg tggaggtgca taatgccaag   660
acaaagccgc gggaggagca gtacaacagc acgtaccgtg tggtcagcgt cctcaccgtc   720
ctgcaccagg actggctgaa tggcaaggag tacaagtgca aggtctccaa caaagccctc   780
ccagccccca tcgagaaaac catctccaaa gccaagggc agccccgaga gccacaggtg   840
tacaccctgc cccatcccg ggatgagctg accaagaacc aggtcagcct gacctgcctg   900
gtcaaaggct ctatcccag cgacatcgcc gtggagtggg agagcaatgg gcagccggag   960
aacaactaca agaccacgcc tcccgtgctg gactccgacg gctccttctt cctctacagc  1020
aagctcaccg tggacaagag caggtggcag caggggaacg tcttctcatg ctccgtgatg  1080
catgaggctc tgcacaacca ctacacgcag aagagcctct ccctgtctcc gggtaaatga  1140
```

<210> SEQ ID NO 14
<211> LENGTH: 870
<212> TYPE: DNA
<213> ORGANISM: H6TEV- K126E/Q133K Dimer -continued

<400> SEQUENCE: 14

```
atgcttctgg ccatggtcct tacctctgcc ctgctcctgt gctccgtggc aggccaaggc      60
catcatcacc atcaccatga ctacgacatc cccaccaccg aaaacctgta cttccagggg     120
tgtccaacct tggcggggat cctggacatc aacttcctca tcaacaagat gcaggaagat     180
ccagcttcca agtgccactg cagtgctaat gtgaccagtt gtctctgttt gggcattccc     240
tctgacaact gcaccagacc atgcttcagt gagagactgt ctcagatgac caataccacc     300
atgcaaacaa gatacccact gattttcagt cgggtgaaaa aatcagttga agtactaaag     360
aacaacaagt gtccatattt ttcctgtgaa cagccatgca accaaaccac ggcaggcaac     420
gcgctgacat ttctggagag tcttctggaa attttcaaga agaaaagat gagagggatg     480
agaggcaaga tacagggtc tccaaccttg gcggggatcc tggacatcaa cttcctcatc     540
aacaagatgc aggaagatcc agcttccaag tgccactgca gtgctaatgt gaccagttgt     600
ctctgtttgg gcattccctc tgacaactgc accagaccat gcttcagtga gagactgtct     660
cagatgacca ataccaccat gcaaacaaga tacccactga ttttcagtcg ggtgaaaaaa     720
tcagttgaag tactaaagaa caacaagtgt ccatattttt cctgtgaaca gccatgcaac     780
caaaccacgg caggcaacgc gctgacattt ctggagagtc ttctggaaat tttcaagaaa     840
gaaaagatga gagggatgag aggcaagata                                      870
```

<210> SEQ ID NO 15
<211> LENGTH: 144
<212> TYPE: PRT
<213> ORGANISM: Wild-type hIL-9

<400> SEQUENCE: 15

```
Met Leu Leu Ala Met Val Leu Thr Ser Ala Leu Leu Leu Cys Ser Val
  1               5                  10                  15

Ala Gly Gln Gly Cys Pro Thr Leu Ala Gly Ile Leu Asp Ile Asn Phe
             20                  25                  30

Leu Ile Asn Lys Met Gln Glu Asp Pro Ala Ser Lys Cys His Cys Ser
         35                  40                  45

Ala Asn Val Thr Ser Cys Leu Cys Leu Gly Ile Pro Ser Asp Asn Cys
     50                  55                  60

Thr Arg Pro Cys Phe Ser Glu Arg Leu Ser Gln Met Thr Asn Thr Thr
 65                  70                  75                  80

Met Gln Thr Arg Tyr Pro Leu Ile Phe Ser Arg Val Lys Lys Ser Val
                 85                  90                  95

Glu Val Leu Lys Asn Asn Lys Cys Pro Tyr Phe Ser Cys Glu Gln Pro
            100                 105                 110

Cys Asn Gln Thr Thr Ala Gly Asn Ala Leu Thr Phe Leu Lys Ser Leu
        115                 120                 125

Leu Glu Ile Phe Gln Lys Glu Lys Met Arg Gly Met Arg Gly Lys Ile
    130                 135                 140
```

<210> SEQ ID NO 16
<211> LENGTH: 270
<212> TYPE: PRT
<213> ORGANISM: Wild-type hIL-9 Dimer

<400> SEQUENCE: 16

```
Met Leu Leu Ala Met Val Leu Thr Ser Ala Leu Leu Leu Cys Ser Val
  1               5                  10                  15
```

-continued

```
Ala Gly Gln Gly Cys Pro Thr Leu Ala Gly Ile Leu Asp Ile Asn Phe
            20                  25                  30

Leu Ile Asn Lys Met Gln Glu Asp Pro Ala Ser Lys Cys His Cys Ser
        35                  40                  45

Ala Asn Val Thr Ser Cys Leu Cys Leu Gly Ile Pro Ser Asp Asn Cys
    50                  55                  60

Thr Arg Pro Cys Phe Ser Glu Arg Leu Ser Gln Met Thr Asn Thr Thr
65                  70                  75                  80

Met Gln Thr Arg Tyr Pro Leu Ile Phe Ser Arg Val Lys Lys Ser Val
                85                  90                  95

Glu Val Leu Lys Asn Asn Lys Cys Pro Tyr Phe Ser Cys Glu Gln Pro
            100                 105                 110

Cys Asn Gln Thr Thr Ala Gly Asn Ala Leu Thr Phe Leu Lys Ser Leu
        115                 120                 125

Leu Glu Ile Phe Gln Lys Glu Lys Met Arg Gly Met Arg Gly Lys Ile
    130                 135                 140

Gln Gly Ser Pro Thr Leu Ala Gly Ile Leu Asp Ile Asn Phe Leu Ile
145                 150                 155                 160

Asn Lys Met Gln Glu Asp Pro Ala Ser Lys Cys His Cys Ser Ala Asn
                165                 170                 175

Val Thr Ser Cys Leu Cys Leu Gly Ile Pro Ser Asp Asn Cys Thr Arg
            180                 185                 190

Pro Cys Phe Ser Glu Arg Leu Ser Gln Met Thr Asn Thr Thr Met Gln
        195                 200                 205

Thr Arg Tyr Pro Leu Ile Phe Ser Arg Val Lys Lys Ser Val Glu Val
    210                 215                 220

Leu Lys Asn Asn Lys Cys Pro Tyr Phe Ser Cys Glu Gln Pro Cys Asn
225                 230                 235                 240

Gln Thr Thr Ala Gly Asn Ala Leu Thr Phe Leu Lys Ser Leu Leu Glu
                245                 250                 255

Ile Phe Gln Lys Glu Lys Met Arg Gly Met Arg Gly Lys Ile
            260                 265                 270

<210> SEQ ID NO 17
<211> LENGTH: 144
<212> TYPE: PRT
<213> ORGANISM: K136D Monomer

<400> SEQUENCE: 17

Met Leu Leu Ala Met Val Leu Thr Ser Ala Leu Leu Cys Ser Val
1               5                   10                  15

Ala Gly Gln Gly Cys Pro Thr Leu Ala Gly Ile Leu Asp Ile Asn Phe
            20                  25                  30

Leu Ile Asn Lys Met Gln Glu Asp Pro Ala Ser Lys Cys His Cys Ser
        35                  40                  45

Ala Asn Val Thr Ser Cys Leu Cys Leu Gly Ile Pro Ser Asp Asn Cys
    50                  55                  60

Thr Arg Pro Cys Phe Ser Glu Arg Leu Ser Gln Met Thr Asn Thr Thr
65                  70                  75                  80

Met Gln Thr Arg Tyr Pro Leu Ile Phe Ser Arg Val Lys Lys Ser Val
                85                  90                  95

Glu Val Leu Lys Asn Asn Lys Cys Pro Tyr Phe Ser Cys Glu Gln Pro
            100                 105                 110

Cys Asn Gln Thr Thr Ala Gly Asn Ala Leu Thr Phe Leu Lys Ser Leu
        115                 120                 125
```

Leu Glu Ile Phe Gln Lys Glu Asp Met Arg Gly Met Arg Gly Lys Ile
            130                 135                 140

<210> SEQ ID NO 18
<211> LENGTH: 270
<212> TYPE: PRT
<213> ORGANISM: K136D Dimer

<400> SEQUENCE: 18

Met Leu Leu Ala Met Val Leu Thr Ser Ala Leu Leu Cys Ser Val
  1               5                  10                  15

Ala Gly Gln Gly Cys Pro Thr Leu Ala Gly Ile Leu Asp Ile Asn Phe
                20                  25                  30

Leu Ile Asn Lys Met Gln Glu Asp Pro Ala Ser Lys Cys His Cys Ser
            35                  40                  45

Ala Asn Val Thr Ser Cys Leu Cys Leu Gly Ile Pro Ser Asp Asn Cys
        50                  55                  60

Thr Arg Pro Cys Phe Ser Glu Arg Leu Ser Gln Met Thr Asn Thr Thr
 65                 70                  75                  80

Met Gln Thr Arg Tyr Pro Leu Ile Phe Ser Arg Val Lys Lys Ser Val
                85                  90                  95

Glu Val Leu Lys Asn Asn Lys Cys Pro Tyr Phe Ser Cys Glu Gln Pro
            100                 105                 110

Cys Asn Gln Thr Thr Ala Gly Asn Ala Leu Thr Phe Leu Lys Ser Leu
        115                 120                 125

Leu Glu Ile Phe Gln Lys Glu Asp Met Arg Gly Met Arg Gly Lys Ile
    130                 135                 140

Gln Gly Ser Pro Thr Leu Ala Gly Ile Leu Asp Ile Asn Phe Leu Ile
145                 150                 155                 160

Asn Lys Met Gln Glu Asp Pro Ala Ser Lys Cys His Cys Ser Ala Asn
                165                 170                 175

Val Thr Ser Cys Leu Cys Leu Gly Ile Pro Ser Asp Asn Cys Thr Arg
            180                 185                 190

Pro Cys Phe Ser Glu Arg Leu Ser Gln Met Thr Asn Thr Thr Met Gln
        195                 200                 205

Thr Arg Tyr Pro Leu Ile Phe Ser Arg Val Lys Lys Ser Val Glu Val
    210                 215                 220

Leu Lys Asn Asn Lys Cys Pro Tyr Phe Ser Cys Glu Gln Pro Cys Asn
225                 230                 235                 240

Gln Thr Thr Ala Gly Asn Ala Leu Thr Phe Leu Lys Ser Leu Leu Glu
                245                 250                 255

Ile Phe Gln Lys Glu Asp Met Arg Gly Met Arg Gly Lys Ile
            260                 265                 270

<210> SEQ ID NO 19
<211> LENGTH: 144
<212> TYPE: PRT
<213> ORGANISM: K134E Monomer

<400> SEQUENCE: 19

Met Leu Leu Ala Met Val Leu Thr Ser Ala Leu Leu Cys Ser Val
  1               5                  10                  15

Ala Gly Gln Gly Cys Pro Thr Leu Ala Gly Ile Leu Asp Ile Asn Phe
                20                  25                  30

Leu Ile Asn Lys Met Gln Glu Asp Pro Ala Ser Lys Cys His Cys Ser
            35                  40                  45

```
Ala Asn Val Thr Ser Cys Leu Cys Leu Gly Ile Pro Ser Asp Asn Cys
     50                  55                  60

Thr Arg Pro Cys Phe Ser Glu Arg Leu Ser Gln Met Thr Asn Thr Thr
 65                  70                  75                  80

Met Gln Thr Arg Tyr Pro Leu Ile Phe Ser Arg Val Lys Lys Ser Val
                 85                  90                  95

Glu Val Leu Lys Asn Asn Lys Cys Pro Tyr Phe Ser Cys Glu Gln Pro
                100                 105                 110

Cys Asn Gln Thr Thr Ala Gly Asn Ala Leu Thr Phe Leu Lys Ser Leu
                115                 120                 125

Leu Glu Ile Phe Gln Glu Glu Lys Met Arg Gly Met Arg Gly Lys Ile
    130                 135                 140

<210> SEQ ID NO 20
<211> LENGTH: 270
<212> TYPE: PRT
<213> ORGANISM: K134E Dimer

<400> SEQUENCE: 20

Met Leu Leu Ala Met Val Leu Thr Ser Ala Leu Leu Leu Cys Ser Val
 1               5                  10                  15

Ala Gly Gln Gly Cys Pro Thr Leu Ala Gly Ile Leu Asp Ile Asn Phe
                 20                  25                  30

Leu Ile Asn Lys Met Gln Glu Asp Pro Ala Ser Lys Cys His Cys Ser
             35                  40                  45

Ala Asn Val Thr Ser Cys Leu Cys Leu Gly Ile Pro Ser Asp Asn Cys
     50                  55                  60

Thr Arg Pro Cys Phe Ser Glu Arg Leu Ser Gln Met Thr Asn Thr Thr
 65                  70                  75                  80

Met Gln Thr Arg Tyr Pro Leu Ile Phe Ser Arg Val Lys Lys Ser Val
                 85                  90                  95

Glu Val Leu Lys Asn Asn Lys Cys Pro Tyr Phe Ser Cys Glu Gln Pro
                100                 105                 110

Cys Asn Gln Thr Thr Ala Gly Asn Ala Leu Thr Phe Leu Lys Ser Leu
                115                 120                 125

Leu Glu Ile Phe Gln Glu Glu Lys Met Arg Gly Met Arg Gly Lys Ile
    130                 135                 140

Gln Gly Ser Pro Thr Leu Ala Gly Ile Leu Asp Ile Asn Phe Leu Ile
145                 150                 155                 160

Asn Lys Met Gln Glu Asp Pro Ala Ser Lys Cys His Cys Ser Ala Asn
                165                 170                 175

Val Thr Ser Cys Leu Cys Leu Gly Ile Pro Ser Asp Asn Cys Thr Arg
            180                 185                 190

Pro Cys Phe Ser Glu Arg Leu Ser Gln Met Thr Asn Thr Thr Met Gln
            195                 200                 205

Thr Arg Tyr Pro Leu Ile Phe Ser Arg Val Lys Lys Ser Val Glu Val
        210                 215                 220

Leu Lys Asn Asn Lys Cys Pro Tyr Phe Ser Cys Glu Gln Pro Cys Asn
225                 230                 235                 240

Gln Thr Thr Ala Gly Asn Ala Leu Thr Phe Leu Lys Ser Leu Leu Glu
                245                 250                 255

Ile Phe Gln Glu Glu Lys Met Arg Gly Met Arg Gly Lys Ile
        260                 265                 270
```

<210> SEQ ID NO 21
<211> LENGTH: 144
<212> TYPE: PRT
<213> ORGANISM: Q133K Monomer

<400> SEQUENCE: 21

```
Met Leu Leu Ala Met Val Leu Thr Ser Ala Leu Leu Cys Ser Val
1               5                   10                  15

Ala Gly Gln Gly Cys Pro Thr Leu Ala Gly Ile Leu Asp Ile Asn Phe
                20                  25                  30

Leu Ile Asn Lys Met Gln Glu Asp Pro Ala Ser Lys Cys His Cys Ser
            35                  40                  45

Ala Asn Val Thr Ser Cys Leu Cys Leu Gly Ile Pro Ser Asp Asn Cys
        50                  55                  60

Thr Arg Pro Cys Phe Ser Glu Arg Leu Ser Gln Met Thr Asn Thr Thr
65                  70                  75                  80

Met Gln Thr Arg Tyr Pro Leu Ile Phe Ser Arg Val Lys Lys Ser Val
                85                  90                  95

Glu Val Leu Lys Asn Asn Lys Cys Pro Tyr Phe Ser Cys Glu Gln Pro
            100                 105                 110

Cys Asn Gln Thr Thr Ala Gly Asn Ala Leu Thr Phe Leu Lys Ser Leu
        115                 120                 125

Leu Glu Ile Phe Lys Lys Glu Lys Met Arg Gly Met Arg Gly Lys Ile
    130                 135                 140
```

<210> SEQ ID NO 22
<211> LENGTH: 270
<212> TYPE: PRT
<213> ORGANISM: Q133K Dimer

<400> SEQUENCE: 22

```
Met Leu Leu Ala Met Val Leu Thr Ser Ala Leu Leu Cys Ser Val
1               5                   10                  15

Ala Gly Gln Gly Cys Pro Thr Leu Ala Gly Ile Leu Asp Ile Asn Phe
                20                  25                  30

Leu Ile Asn Lys Met Gln Glu Asp Pro Ala Ser Lys Cys His Cys Ser
            35                  40                  45

Ala Asn Val Thr Ser Cys Leu Cys Leu Gly Ile Pro Ser Asp Asn Cys
        50                  55                  60

Thr Arg Pro Cys Phe Ser Glu Arg Leu Ser Gln Met Thr Asn Thr Thr
65                  70                  75                  80

Met Gln Thr Arg Tyr Pro Leu Ile Phe Ser Arg Val Lys Lys Ser Val
                85                  90                  95

Glu Val Leu Lys Asn Asn Lys Cys Pro Tyr Phe Ser Cys Glu Gln Pro
            100                 105                 110

Cys Asn Gln Thr Thr Ala Gly Asn Ala Leu Thr Phe Leu Lys Ser Leu
        115                 120                 125

Leu Glu Ile Phe Lys Lys Glu Lys Met Arg Gly Met Arg Gly Lys Ile
    130                 135                 140

Gln Gly Ser Pro Thr Leu Ala Gly Ile Leu Asp Ile Asn Phe Leu Ile
145                 150                 155                 160

Asn Lys Met Gln Glu Asp Pro Ala Ser Lys Cys His Cys Ser Ala Asn
                165                 170                 175

Val Thr Ser Cys Leu Cys Leu Gly Ile Pro Ser Asp Asn Cys Thr Arg
            180                 185                 190

Pro Cys Phe Ser Glu Arg Leu Ser Gln Met Thr Asn Thr Thr Met Gln
```

-continued

```
                195                 200                 205
Thr Arg Tyr Pro Leu Ile Phe Ser Arg Val Lys Lys Ser Val Glu Val
    210                 215                 220

Leu Lys Asn Asn Lys Cys Pro Tyr Phe Ser Cys Glu Gln Pro Cys Asn
225                 230                 235                 240

Gln Thr Thr Ala Gly Asn Ala Leu Thr Phe Leu Lys Ser Leu Leu Glu
                245                 250                 255

Ile Phe Lys Lys Glu Lys Met Arg Gly Met Arg Gly Lys Ile
            260                 265                 270

<210> SEQ ID NO 23
<211> LENGTH: 396
<212> TYPE: PRT
<213> ORGANISM: Q133K Trimer

<400> SEQUENCE: 23

Met Leu Leu Ala Met Val Leu Thr Ser Ala Leu Leu Cys Ser Val
  1               5                  10                  15

Ala Gly Gln Gly Cys Pro Thr Leu Ala Gly Ile Leu Asp Ile Asn Phe
                20                  25                  30

Leu Ile Asn Lys Met Gln Glu Asp Pro Ala Ser Lys Cys His Cys Ser
            35                  40                  45

Ala Asn Val Thr Ser Cys Leu Cys Leu Gly Ile Pro Ser Asp Asn Cys
        50                  55                  60

Thr Arg Pro Cys Phe Ser Glu Arg Leu Ser Gln Met Thr Asn Thr Thr
65                  70                  75                  80

Met Gln Thr Arg Tyr Pro Leu Ile Phe Ser Arg Val Lys Lys Ser Val
                85                  90                  95

Glu Val Leu Lys Asn Asn Lys Cys Pro Tyr Phe Ser Cys Glu Gln Pro
                100                 105                 110

Cys Asn Gln Thr Thr Ala Gly Asn Ala Leu Thr Phe Leu Lys Ser Leu
            115                 120                 125

Leu Glu Ile Phe Lys Lys Glu Lys Met Arg Gly Met Arg Gly Lys Ile
    130                 135                 140

Gln Gly Ser Pro Thr Leu Ala Gly Ile Leu Asp Ile Asn Phe Leu Ile
145                 150                 155                 160

Asn Lys Met Gln Glu Asp Pro Ala Ser Lys Cys His Cys Ser Ala Asn
                165                 170                 175

Val Thr Ser Cys Leu Cys Leu Gly Ile Pro Ser Asp Asn Cys Thr Arg
                180                 185                 190

Pro Cys Phe Ser Glu Arg Leu Ser Gln Met Thr Asn Thr Thr Met Gln
            195                 200                 205

Thr Arg Tyr Pro Leu Ile Phe Ser Arg Val Lys Lys Ser Val Glu Val
    210                 215                 220

Leu Lys Asn Asn Lys Cys Pro Tyr Phe Ser Cys Glu Gln Pro Cys Asn
225                 230                 235                 240

Gln Thr Thr Ala Gly Asn Ala Leu Thr Phe Leu Lys Ser Leu Leu Glu
                245                 250                 255

Ile Phe Lys Lys Glu Lys Met Arg Gly Met Arg Gly Lys Ile Gln Gly
            260                 265                 270

Ser Pro Thr Leu Ala Gly Ile Leu Asp Ile Asn Phe Leu Ile Asn Lys
        275                 280                 285

Met Gln Glu Asp Pro Ala Ser Lys Cys His Cys Ser Ala Asn Val Thr
    290                 295                 300
```

```
Ser Cys Leu Cys Leu Gly Ile Pro Ser Asp Asn Cys Thr Arg Pro Cys
305                 310                 315                 320

Phe Ser Glu Arg Leu Ser Gln Met Thr Asn Thr Thr Met Gln Thr Arg
            325                 330                 335

Tyr Pro Leu Ile Phe Ser Arg Val Lys Lys Ser Val Glu Val Leu Lys
                340                 345                 350

Asn Asn Lys Cys Pro Tyr Phe Ser Cys Glu Gln Pro Cys Asn Gln Thr
            355                 360                 365

Thr Ala Gly Asn Ala Leu Thr Phe Leu Lys Ser Leu Leu Glu Ile Phe
        370                 375                 380

Lys Lys Glu Lys Met Arg Gly Met Arg Gly Lys Ile
385                 390                 395

<210> SEQ ID NO 24
<211> LENGTH: 144
<212> TYPE: PRT
<213> ORGANISM: K126E/Q133K Monomer

<400> SEQUENCE: 24

Met Leu Leu Ala Met Val Leu Thr Ser Ala Leu Leu Cys Ser Val
1               5                   10                  15

Ala Gly Gln Gly Cys Pro Thr Leu Ala Gly Ile Leu Asp Ile Asn Phe
            20                  25                  30

Leu Ile Asn Lys Met Gln Glu Asp Pro Ala Ser Lys Cys His Cys Ser
        35                  40                  45

Ala Asn Val Thr Ser Cys Leu Cys Leu Gly Ile Pro Ser Asp Asn Cys
    50                  55                  60

Thr Arg Pro Cys Phe Ser Glu Arg Leu Ser Gln Met Thr Asn Thr Thr
65                  70                  75                  80

Met Gln Thr Arg Tyr Pro Leu Ile Phe Ser Arg Val Lys Lys Ser Val
                85                  90                  95

Glu Val Leu Lys Asn Asn Lys Cys Pro Tyr Phe Ser Cys Glu Gln Pro
            100                 105                 110

Cys Asn Gln Thr Thr Ala Gly Asn Ala Leu Thr Phe Leu Glu Ser Leu
        115                 120                 125

Leu Glu Ile Phe Lys Lys Glu Lys Met Arg Gly Met Arg Gly Lys Ile
    130                 135                 140

<210> SEQ ID NO 25
<211> LENGTH: 270
<212> TYPE: PRT
<213> ORGANISM: K126E/Q133K Dimer

<400> SEQUENCE: 25

Met Leu Leu Ala Met Val Leu Thr Ser Ala Leu Leu Cys Ser Val
1               5                   10                  15

Ala Gly Gln Gly Cys Pro Thr Leu Ala Gly Ile Leu Asp Ile Asn Phe
            20                  25                  30

Leu Ile Asn Lys Met Gln Glu Asp Pro Ala Ser Lys Cys His Cys Ser
        35                  40                  45

Ala Asn Val Thr Ser Cys Leu Cys Leu Gly Ile Pro Ser Asp Asn Cys
    50                  55                  60

Thr Arg Pro Cys Phe Ser Glu Arg Leu Ser Gln Met Thr Asn Thr Thr
65                  70                  75                  80

Met Gln Thr Arg Tyr Pro Leu Ile Phe Ser Arg Val Lys Lys Ser Val
                85                  90                  95
```

```
Glu Val Leu Lys Asn Asn Lys Cys Pro Tyr Phe Ser Cys Glu Gln Pro
            100                 105                 110

Cys Asn Gln Thr Thr Ala Gly Asn Ala Leu Thr Phe Leu Glu Ser Leu
        115                 120                 125

Leu Glu Ile Phe Lys Lys Glu Lys Met Arg Gly Met Arg Gly Lys Ile
    130                 135                 140

Gln Gly Ser Pro Thr Leu Ala Gly Ile Leu Asp Ile Asn Phe Leu Ile
145                 150                 155                 160

Asn Lys Met Gln Glu Asp Pro Ala Ser Lys Cys His Cys Ser Ala Asn
                165                 170                 175

Val Thr Ser Cys Leu Cys Leu Gly Ile Pro Ser Asp Asn Cys Thr Arg
            180                 185                 190

Pro Cys Phe Ser Glu Arg Leu Ser Gln Met Thr Asn Thr Thr Met Gln
        195                 200                 205

Thr Arg Tyr Pro Leu Ile Phe Ser Arg Val Lys Lys Ser Val Glu Val
    210                 215                 220

Leu Lys Asn Asn Lys Cys Pro Tyr Phe Ser Cys Glu Gln Pro Cys Asn
225                 230                 235                 240

Gln Thr Thr Ala Gly Asn Ala Leu Thr Phe Leu Glu Ser Leu Leu Glu
                245                 250                 255

Ile Phe Lys Lys Glu Lys Met Arg Gly Met Arg Gly Lys Ile
            260                 265                 270

<210> SEQ ID NO 26
<211> LENGTH: 382
<212> TYPE: PRT
<213> ORGANISM: Fc-K126E/Q133K

<400> SEQUENCE: 26

Met Glu Thr Asp Thr Leu Leu Leu Trp Val Leu Leu Leu Trp Val Pro
1               5                   10                  15

Gly Ser Ile Gly Glu Ser Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205
```

-continued

```
Phe Phe Leu Tyr Ser Lys Leu Thr Val Asp Lys Ser Arg Trp Gln Gln
        210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Ala Ala Ala Gly
                245                 250                 255

Gln Gly Cys Pro Thr Leu Ala Gly Ile Leu Asp Ile Asn Phe Leu Ile
                260                 265                 270

Asn Lys Met Gln Glu Asp Pro Ala Ser Lys Cys His Cys Ser Ala Asn
            275                 280                 285

Val Thr Ser Cys Leu Cys Leu Gly Ile Pro Ser Asp Asn Cys Thr Arg
        290                 295                 300

Pro Cys Phe Ser Glu Arg Leu Ser Gln Met Thr Asn Thr Thr Met Gln
305                 310                 315                 320

Thr Arg Tyr Pro Leu Ile Phe Ser Arg Val Lys Lys Ser Val Glu Val
                325                 330                 335

Leu Lys Asn Asn Lys Cys Pro Tyr Phe Ser Cys Glu Gln Pro Cys Asn
                340                 345                 350

Gln Thr Thr Ala Gly Asn Ala Leu Thr Phe Leu Glu Ser Leu Leu Glu
            355                 360                 365

Ile Phe Lys Lys Glu Lys Met Arg Gly Met Arg Gly Lys Ile
        370                 375                 380

<210> SEQ ID NO 27
<211> LENGTH: 379
<212> TYPE: PRT
<213> ORGANISM: K126E/Q133K-Fc

<400> SEQUENCE: 27

Met Leu Leu Ala Met Val Leu Thr Ser Ala Leu Leu Leu Cys Ser Val
1               5                   10                  15

Ala Gly Gln Gly Cys Pro Thr Leu Ala Gly Ile Leu Asp Ile Asn Phe
                20                  25                  30

Leu Ile Asn Lys Met Gln Glu Asp Pro Ala Ser Lys Cys His Cys Ser
            35                  40                  45

Ala Asn Val Thr Ser Cys Leu Cys Leu Gly Ile Pro Ser Asp Asn Cys
        50                  55                  60

Thr Arg Pro Cys Phe Ser Glu Arg Leu Ser Gln Met Thr Asn Thr Thr
65                  70                  75                  80

Met Gln Thr Arg Tyr Pro Leu Ile Phe Ser Arg Val Lys Lys Ser Val
                85                  90                  95

Glu Val Leu Lys Asn Asn Lys Cys Pro Tyr Phe Ser Cys Glu Gln Pro
                100                 105                 110

Cys Asn Gln Thr Thr Ala Gly Asn Ala Leu Thr Phe Leu Glu Ser Leu
            115                 120                 125

Leu Glu Ile Phe Lys Lys Glu Lys Met Arg Gly Met Arg Gly Lys Ile
        130                 135                 140

Ala Ala Ala Glu Ser Lys Ser Cys Asp Lys Thr His Thr Cys Pro Pro
145                 150                 155                 160

Cys Pro Ala Pro Glu Leu Leu Gly Gly Pro Ser Val Phe Leu Phe Pro
                165                 170                 175

Pro Lys Pro Lys Asp Thr Leu Met Ile Ser Arg Thr Pro Glu Val Thr
            180                 185                 190

Cys Val Val Val Asp Val Ser His Glu Asp Pro Glu Val Lys Phe Asn
```

```
                    195                 200                 205
Trp Tyr Val Asp Gly Val Glu Val His Asn Ala Lys Thr Lys Pro Arg
    210                 215                 220

Glu Glu Gln Tyr Asn Ser Thr Tyr Arg Val Val Ser Val Leu Thr Val
225                 230                 235                 240

Leu His Gln Asp Trp Leu Asn Gly Lys Glu Tyr Lys Cys Lys Val Ser
                245                 250                 255

Asn Lys Ala Leu Pro Ala Pro Ile Glu Lys Thr Ile Ser Lys Ala Lys
            260                 265                 270

Gly Gln Pro Arg Glu Pro Gln Val Tyr Thr Leu Pro Pro Ser Arg Asp
        275                 280                 285

Glu Leu Thr Lys Asn Gln Val Ser Leu Thr Cys Leu Val Lys Gly Phe
    290                 295                 300

Tyr Pro Ser Asp Ile Ala Val Glu Trp Glu Ser Asn Gly Gln Pro Glu
305                 310                 315                 320

Asn Asn Tyr Lys Thr Thr Pro Pro Val Leu Asp Ser Asp Gly Ser Phe
                325                 330                 335

Phe Leu Tyr Ser Lys Leu Thr Val Asp Lys Ser Arg Trp Gln Gln Gly
            340                 345                 350

Asn Val Phe Ser Cys Ser Val Met His Glu Ala Leu His Asn His Tyr
        355                 360                 365

Thr Gln Lys Ser Leu Ser Leu Ser Pro Gly Lys
    370                 375

<210> SEQ ID NO 28
<211> LENGTH: 290
<212> TYPE: PRT
<213> ORGANISM: Uncleaved TEV K126E/Q133K Dimer

<400> SEQUENCE: 28

Met Leu Leu Ala Met Val Leu Thr Ser Ala Leu Leu Leu Cys Ser Val
1               5                   10                  15

Ala Gly Gln Gly His His His His His Asp Tyr Asp Ile Pro Thr
            20                  25                  30

Thr Glu Asn Leu Tyr Phe Gln Gly Cys Pro Thr Leu Ala Gly Ile Leu
        35                  40                  45

Asp Ile Asn Phe Leu Ile Asn Lys Met Gln Glu Asp Pro Ala Ser Lys
    50                  55                  60

Cys His Cys Ser Ala Asn Val Thr Ser Cys Leu Cys Leu Gly Ile Pro
65                  70                  75                  80

Ser Asp Asn Cys Thr Arg Pro Cys Phe Ser Glu Arg Leu Ser Gln Met
                85                  90                  95

Thr Asn Thr Thr Met Gln Thr Arg Tyr Pro Leu Ile Phe Ser Arg Val
            100                 105                 110

Lys Lys Ser Val Glu Val Leu Lys Asn Asn Lys Cys Pro Tyr Phe Ser
        115                 120                 125

Cys Glu Gln Pro Cys Asn Gln Thr Thr Ala Gly Asn Ala Leu Thr Phe
    130                 135                 140

Leu Glu Ser Leu Leu Glu Ile Phe Lys Lys Glu Lys Met Arg Gly Met
145                 150                 155                 160

Arg Gly Lys Ile Gln Gly Ser Pro Thr Leu Ala Gly Ile Leu Asp Ile
                165                 170                 175

Asn Phe Leu Ile Asn Lys Met Gln Glu Asp Pro Ala Ser Lys Cys His
            180                 185                 190
```

```
Cys Ser Ala Asn Val Thr Ser Cys Leu Cys Leu Gly Ile Pro Ser Asp
        195                 200                 205

Asn Cys Thr Arg Pro Cys Phe Ser Glu Arg Leu Ser Gln Met Thr Asn
    210                 215                 220

Thr Thr Met Gln Thr Arg Tyr Pro Leu Ile Phe Ser Arg Val Lys Lys
225                 230                 235                 240

Ser Val Glu Val Leu Lys Asn Asn Lys Cys Pro Tyr Phe Ser Cys Glu
                245                 250                 255

Gln Pro Cys Asn Gln Thr Thr Ala Gly Asn Ala Leu Thr Phe Leu Glu
            260                 265                 270

Ser Leu Leu Glu Ile Phe Lys Lys Glu Lys Met Arg Gly Met Arg Gly
        275                 280                 285

Lys Ile
    290

<210> SEQ ID NO 29
<211> LENGTH: 251
<212> TYPE: PRT
<213> ORGANISM: Cleaved TEV K126E/Q133K Dimer

<400> SEQUENCE: 29

Gly Cys Pro Thr Leu Ala Gly Ile Leu Asp Ile Asn Phe Leu Ile Asn
1               5                   10                  15

Lys Met Gln Glu Asp Pro Ala Ser Lys Cys His Cys Ser Ala Asn Val
            20                  25                  30

Thr Ser Cys Leu Cys Leu Gly Ile Pro Ser Asp Asn Cys Thr Arg Pro
        35                  40                  45

Cys Phe Ser Glu Arg Leu Ser Gln Met Thr Asn Thr Thr Met Gln Thr
    50                  55                  60

Arg Tyr Pro Leu Ile Phe Ser Arg Val Lys Lys Ser Val Glu Val Leu
65                  70                  75                  80

Lys Asn Asn Lys Cys Pro Tyr Phe Ser Cys Glu Gln Pro Cys Asn Gln
                85                  90                  95

Thr Thr Ala Gly Asn Ala Leu Thr Phe Leu Glu Ser Leu Leu Glu Ile
            100                 105                 110

Phe Lys Lys Glu Lys Met Arg Gly Met Arg Gly Lys Ile Gln Gly Ser
        115                 120                 125

Pro Thr Leu Ala Gly Ile Leu Asp Ile Asn Phe Leu Ile Asn Lys Met
    130                 135                 140

Gln Glu Asp Pro Ala Ser Lys Cys His Cys Ser Ala Asn Val Thr Ser
145                 150                 155                 160

Cys Leu Cys Leu Gly Ile Pro Ser Asp Asn Cys Thr Arg Pro Cys Phe
                165                 170                 175

Ser Glu Arg Leu Ser Gln Met Thr Asn Thr Thr Met Gln Thr Arg Tyr
            180                 185                 190

Pro Leu Ile Phe Ser Arg Val Lys Lys Ser Val Glu Val Leu Lys Asn
        195                 200                 205

Asn Lys Cys Pro Tyr Phe Ser Cys Glu Gln Pro Cys Asn Gln Thr Thr
    210                 215                 220

Ala Gly Asn Ala Leu Thr Phe Leu Glu Ser Leu Leu Glu Ile Phe Lys
225                 230                 235                 240

Lys Glu Lys Met Arg Gly Met Arg Gly Lys Ile
                245                 250
```

INTERLEUKIN-9 ANTAGONIST MUTEINS AND THEIR PHARMACOLOGICAL METHODS OF USE

This application claims the benefit of and incorporates by reference co-pending provisional application Ser. No. 60/470,630 filed May 14, 2003.

FIELD OF THE INVENTION

The invention relates to the field of pulmonary disease therapy. More particularly, the invention relates to the use of Interleukin-9 (IL-9) muteins as therapeutic agents. The invention also relates to the use of IL-9 muteins, compositions, and methods to provide treatment options for individuals afflicted with conditions where inhibiting IL-9 mediated immune responses would be beneficial.

BACKGROUND OF THE INVENTION

Interleukin-9 (IL-9) is a pleiotrophic cytokine produced by activated T cells upon antigen stimulation and was first described in the mouse as a T-cell growth factor. IL-9 has a two subunit receptor that consists of IL-9R$\alpha$ and the common $\gamma$ chain, which is a shared component of the receptor complexes for IL-2, IL-4, IL-7, IL-13, IL-15 and possibly others.

A number of studies suggest that IL-9, as a mediator of Th2-dependent immune responses, may play a role in asthma. The IL-9 gene resides within the Th2 cytokine cluster on chromosome 5q. Linkage analysis shows an association between the IL-9 gene and elevated serum levels of IgE production and airway hyper-responsiveness. IL-9 transgenic mice exhibit many characteristics of human asthma: airway eosinophilia, elevated serum IgE and bronchial hyper-responsiveness. These transgenic mice have a strikingly robust peribronchial and perivascular eosinophilia after allergen challenge. The eosinophilia was shown to be coincident with the upregulation in lung epithelial cells of eotaxin, MIP-1 and MCP-1, -3, -5, which are chemotactic for eosinophils.

Expression of the IL-9 receptor on mature peripheral eosinophils has been demonstrated and IL-9 inhibits eosinophil apoptosis in a concentration dependent manner. It is also known that other cell types in the lung, i.e., alveolar macrophages and mast cells, when stimulated with IL-9 also produce chemokines. Other evidence for the role of IL-9 in asthma includes studies of the ability of IL-9 to stimulate mucin secretion by airway epithelial cells. The above studies taken together illustrate and support the role of IL-9 in regulating many clinical hallmarks of asthma and allergic inflammation.

Decreased IL-9 activity will have the beneficial effects of decreasing Th2 polarization of the T-cell response, decreasing eosinophil survival and neutrophil activity, and attenuating mucus production by airway epithelial cells. This will, in turn, reduce airway hyperreactivity and remodelling while increasing gas exchange and clearance, thus providing an effective therapeutic modality for several lung diseases including asthma, chronic obstructive pulmonary disease (emphysema and chronic bronchitis), and related pulmonary conditions.

IL-9 has also been shown to be a major anti-apoptotic factor for thymic lymphomas and may also contribute to the proliferation of other leukemias through its actions as an autocrine growth factor. Decreased IL-9 activity in patients with several types of leukemia will have the beneficial effect of slowing the cancerous growth and possibly enhancing the effects of other cancer therapies.

One method for attenuating IL-9-mediated activity is to inhibit cytokine signaling through its cognate cell-surface receptor. This can be achieved with bioengineered IL-9 antagonists. The engineered muteins would competitively inhibit the ability of wild-type IL-9 to signal by blocking its binding to the receptor.

SUMMARY OF THE INVENTION

It is an object of the invention to provide reagents and methods of inhibiting IL-9-mediated immune responses. This and other objects of the invention are provided by one or more of the embodiments listed below.

In one embodiment, the invention provides a purified preparation of an IL-9 mutein numbered in accordance with wild type IL-9 wherein said mutein is an IL-9 antagonist and comprises at least one amino-acid substitution. In one aspect of this embodiment, the purified preparation comprises a IL-9 mutein receptor antagonist polypeptide that is encoded by a nucleotide sequence as set forth in SEQ ID NOS: 3-14. In another aspect, the polypeptide comprises an amino acid sequence as set forth in SEQ ID NOS: 17-29. In additional aspects of this embodiment, the invention provides a purified IL-9 mutein receptor antagonist wherein glutamine is replaced by lysine at position 133 (SEQ ID NO. 21), lysine is replaced by glutamate at position 134 (SEQ ID NO. 19), lysine is replaced by aspartate at position 136 (SEQ ID NO. 17) or lysine is replaced by glutamate at position 126 and at position 133 glutamine is replaced by lysine (SEQ ID NO. 24).

In another embodiment, the invention provides a purified preparation of an IL-9 mutein receptor anatgonist multimer comprising two or more IL-9 muteins of the invention fused C-terminus to N-terminus to form the multimer as set forth in SEQ ID NOS. 18, 20, 22, 23, 25, 28 and 29.

In an additional embodiment, the invention provides a purified preparation of a fusion protein comprised of an Fc region of an immunoglobulin molecule fused to the N-terminus or C-terminus of an IL-9 mutein receptor antagonist as set forth in SEQ ID NOS. 26 and 27, respectively.

In one embodiment, the IL-9 mutein receptor antagonist of the invention binds to the IL-9 receptor with a Kd of about 0.1 nM to about 10 $\mu$M, or preferably of about 0.5 nM to about 1 $\mu$M, or most preferably about 1.0 $\mu$M to about 100 $\mu$M.

In another embodiment, the IL-9 mutein receptor antagonist inhibits the proliferative response of Mo7E cells to IL-9 with an IC50 value of about 0.1 nM to about 10 $\mu$M, or preferably of about 0.5 nM to about 1 $\mu$M, or most preferably about 1.0 nM to about 100 nM.

In still another embodiment, the IL-9 mutein inhibits the anti-apoptotic response of eosinophils to IL-9 with an IC50 value of about 0.1 nM to about 10 $\mu$M, or preferably of about 0.5 nM to about 1 $\mu$M, or most preferably about 1.0 nM to about 100 nM.

The invention also provides pharmaceutical compositions comprising: (a) a IL-9 mutein receptor antagonist which binds to the human IL-9 receptor; and (b) a pharmaceutically acceptable carrier.

The invention also provides a purified polynucleotide comprising (a) a nucleotide sequence as set forth in SEQ ID NO: 3-14 or (b) a polynucleotide sequence encoding a polypeptide having an amino acid sequence as set forth in SEQ ID NO: 17-29.

The invention also provides expression vectors comprising a polynucleotide of the invention and host cells comprising an expression vector of the invention.

In addition, the invention provides methods of making an IL-9 mutein receptor antagonist, comprising the steps of: (a) culturing the host cell described above under conditions whereby the antagonist is expressed; and (b) purifying the antagonist from the host cell culture. In a particular aspect, an antagonist produced by a method of the invention can inhibit IL-9-mediated activity.

The invention also provides methods for treating a human disorder associated with increased activity of IL-9 comprising the steps of: (a) providing a human having a condition in which activity of IL-9 is increased; and (b) administering to said human an effective amount of modified IL-9 mutein receptor antagonist of the invention or a pharmaceutical composition of the invention. In one aspect, the disorder is asthma, chronic obstructive pulmonary disease (such as emphysema or chronic bronchitis), or related pulmonary conditions.

The invention also provides a method of preparing a modified IL-9 mutein receptor antagonist in active form, antagonists prepared by the method, compositions comprising such antagonists and method of treating human disorders comprising administering such antagonists, and pharmaceutical compositions including such antagonists. The method comprises the steps of: (a) culturing the host cell as described above under conditions whereby the antagonist is expressed and (b) expressing and purifying the antagonist from the host cell culture.

Additionally, the invention provides methods of purifying polypeptides expressed from eukaryotic cells. In one aspect of this technology, a nucleotide that encodes a signal sequence is joined to a nucleotide that encodes a protein of interest (in one example, the protein of interest is an IL-9 mutein). When the combination nucleotide is inserted into a eukaryotic cell and then expressed, the secreted protein will include the tag sequence. In another aspect of this technology, a nucleotide encoding a digestible linker sequence (in one example, the digestible linker sequence is digested by TEV protease) is inserted between the nucleotide encoding the protein of interest and the nucleotide which encodes the tag sequence. In both of the above examples, once the protein of interest is expressed from a eukaryotic cell, the protein of interest can be isolated by selecting a resin having affinity for the tag sequence (in one example, His6 was used). For those proteins having a digestible linker between the protein of interest and the tag sequence, the protein of interest, once isolated on the resin, can be removed through the use of an enzyme that digests the linker sequence.

Specific preferred embodiments of the present invention will become evident from the following more detailed description of certain preferred embodiments and the claims.

BRIEF DESCRIPTION OF THE FIGURES

FIG. 1. Polynucleotide Sequences of SEQ ID NOs.: 1 through 14.

FIG. 2. Polypeptide Sequences of SEQ ID NOs.: 15 through 29.

FIG. 3. Mo7E Proliferation Assay Agonism Results

FIG. 4. Mo7E Proliferation Assay Antagonism Results

FIG. 5. Eosinophil Survival Assay Results

DETAILED DESCRIPTION OF THE INVENTION

This invention relates to IL-9 mutein receptor antagonists. Unless otherwise required by context, singular terms shall include pluralities and plural terms shall include the singular.

The section headings used herein are for organizational purposes only and are not to be construed as limiting the subject matter described. All references cited in this application are expressly incorporated by reference herein.

DEFINITIONS

The term "polynucleotide" or "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "purified" or "isolated" polynucleotide refers to a nucleic acid molecule of the invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use.

By "numbered in accordance with wild type IL-9" we mean identifying a chosen amino acid with reference to the position at which that amino acid normally occurs in wild type IL-9.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "host cell" is used herein to refer to a cell that has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "resin" is used to refer to a durable immobilized metal affinity resin that has an affinity and specificity for His-tagged proteins. The metal ion used with these resins is normally nickel, although other metal ions such as cobalt can be used.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., Molecular Cloning, A Laboratory Manual (Cold Spring Harbor Laboratories, 1989); Davis et al., Basic Methods in Molecular Biology (Elsevier, 1986); and Chu et al., 1981, Gene 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

The term "identity," as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is a related concept, but in contrast to "identity," "similarity" refers to a measure of relatedness which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

Identity and similarity of related nucleic acids and polypeptides can be readily calculated by known methods. Such methods include, but are not limited to, those described in COMPUTATIONAL MOLECULAR BIOLOGY, (Lesk, A. M., ed.), 1988, Oxford University Press, New York; BIOCOMPUTING: INFORMATICS AND GENOME PROJECTS, (Smith, D. W., ed.), 1993, Academic Press, New York; COMPUTER ANALYSIS OF SEQUENCE DATA, Part 1, (Griffin, A. M., and Griffin, H. G., eds.), 1994, Humana Press, New Jersey; von Heinje, G., SEQUENCE ANALYSIS IN MOLECULAR BIOLOGY, 1987, Academic Press; SEQUENCE ANALYSIS PRIMER, (Gribskov, M. and Devereux, J., eds.), 1991, M. Stockton Press, New York; Carillo et al., 1988, SIAM J. Applied Math., 48:1073; and Durbin et al., 1998, BIOLOGICAL SEQUENCE ANALYSIS, Cambridge University Press.

Preferred methods to determine identity are designed to give the largest match between the sequences tested. Methods to determine identity are described in publicly available computer programs. Preferred computer program methods to determine identity between two sequences include, but are not limited to, the GCG program package, including GAP (Devereux et al., 1984, Nucl. Acid. Res., 12:387; Genetics Computer Group, University of Wisconsin, Madison, Wis.), BLASTP, BLASTN, and FASTA (Altschul et al., 1990, J. Mol. Biol., 215:403-410). The BLASTX program is publicly available from the National Center for Biotechnology Information (NCBI) and other sources (BLAST Manual, Altschul et al. NCB/NLM/NIH Bethesda, Md. 20894; Altschul et al., 1990, supra). The well-known Smith Waterman algorithm may also be used to determine identity.

Certain alignment schemes for aligning two amino acid sequences may result in matching of only a short region of the two sequences, and this small aligned region may have very high sequence identity even though there is no significant relationship between the two full-length sequences. Accordingly, in certain embodiments, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is calculated as three-times the average diagonal; where the "average diagonal" is the average of the diagonal of the comparison matrix being used; the "diagonal" is the score or number assigned to each perfect amino acid match by the particular comparison matrix) and a gap extension penalty (which is usually one-tenth of the gap opening penalty), as well as a comparison matrix such as PAM250 or BLOSUM 62 are used in conjunction with the algorithm. In certain embodiments, a standard comparison matrix (see Dayhoff et al., 1978, Atlas of Protein Sequence and Structure, 5:345-352 for the PAM 250 comparison matrix; Henikoff et al., 1992, Proc. Natl. Acad. Sci. USA, 89:10915-10919 for the BLOSUM 62 comparison matrix) is also used by the algorithm.

In certain embodiments, the parameters for a polypeptide sequence comparison include the following: Algorithm: Needleman et al., 1970, J. Mol. Biol., 48:443-453; Comparison matrix: BLOSUM 62 from Henikoff et al., 1992, supra; Gap Penalty: 12, Gap Length Penalty: 4, Threshold of Similarity: 0

The GAP program may be useful with the above parameters. In certain embodiments, the aforementioned parameters are the default parameters for polypeptide comparisons (along with no penalty for end gaps) using the GAP algorithm.

As used herein, the twenty conventional amino acids and their abbreviations follow conventional usage. See IMMUNOLOGY—A SYNTHESIS, 2nd Edition, (E. S. Golub and D. R. Gren, Eds.), Sinauer Associates: Sunderland, Mass., 1991, incorporated herein by reference for any purpose. Stereoisomers (e.g., d-amino acids) of the twenty conventional amino acids; unnatural amino acids such as α-, α-disubstituted amino acids, N-alkyl amino acids, lactic acid, and other unconventional amino acids may also be suitable components for polypeptides of the invention. Examples of unconventional amino acids include: 4-hydroxyproline, γ-carboxyglutamate, ε—N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

Naturally occurring residues may be divided into classes based on common side chain properties:

1) hydrophobic: norleucine (Nor), Met, Ala, Val, Leu, Ile;
2) neutral hydrophilic: Cys, Ser, Thr, Asn, Gln;
3) acidic: Asp, Glu;
4) basic: H is, Lys, Arg;
5) residues that influence chain orientation: Gly, Pro; and
6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of these classes for a member from another class. Such substituted residues may be introduced into regions of a human protein that are homologous with non-human proteins, or into the non-homologous regions of the molecule.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those that are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of a polypeptide with respect to its three dimensional structure. In certain embodiments, one skilled in the art may choose to not make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult, 1996, Curr. Op. in Biotech. 7:422-427; Chou et al., 1974, Biochemistry 13:222-245; Chou et al., 1974, Biochemistry 113:211-222; Chou et al., 1978, Adv. Enzymol. Relat. Areas Mol. Biol. 47:45-148; Chou et al., 1979, Ann. Rev. Biochem. 47:251-276; and Chou et al., 1979, Biophys. J. 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., 1999, Nucl. Acid. Res. 27:244-247. It has been suggested (Brenner et al., 1997, Curr. Op. Struct. Biol. 7:369-376) that there are a limited number of folds in a given polypeptide or protein and that once a critical number of structures have been resolved, structural prediction will become dramatically more accurate.

Additional methods of predicting secondary structure include "threading" (Jones, 1997, Curr. Opin. Struct. Biol. 7:377-87; Sippl et al., 1996, Structure 4:15-19), "profile analysis" (Bowie et al., 1991, Science 253:164-170; Gribskov et al., 1990, Meth. Enzym. 183:146-159; Gribskov et al., 1987, Proc. Nat. Acad. Sci. 84:4355-4358), and "evolutionary linkage" (See Holm, 1999, supra; and Brenner, 1997, supra).

In certain embodiments, protein variants include glycosylation variants wherein the number and/or type of glycosylation site has been altered compared to the amino acid sequences of the parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred variants include cysteine variants wherein one or more cysteine residues are deleted from or substituted for another amino acid (e.g., serine) compared to the parent amino acid sequence. Cysteine variants may be useful when proteins must be refolded into a biologically active conformation such as after the isolation of insoluble inclusion bodies. Cysteine variants generally have fewer cysteine residues than the native protein, and typically have an even number to minimize interactions resulting from unpaired cysteines.

In additional embodiments, protein variants can include mutations such as substitutions, additions, deletions, or any combination thereof, and are typically produced by site-directed mutagenesis using one or more mutagenic oligonucleotide(s) according to methods described herein, as well as according to methods known in the art (see, for example, Sambrook et al., MOLECULAR CLONING: A LABORATORY MANUAL, 3rd Ed., 2001, Cold Spring Harbor, N.Y. and Berger and Kimmel, METHODS IN ENZYMOLOGY, Volume 152, Guide to Molecular Cloning Techniques, 1987, Academic Press, Inc., San Diego, Calif., which are incorporated herein by reference).

According to certain embodiments, amino acid substitutions are those that: (1) reduce susceptibility to proteolysis, (2) reduce susceptibility to oxidation, (3) alter binding affinity for forming protein complexes, (4) alter binding affinities, and/or (5) confer or modify other physicochemical or functional properties on such polypeptides. According to certain embodiments, single or multiple amino acid substitutions (in certain embodiments, conservative amino acid substitutions) may be made in the naturally occurring sequence (in certain embodiments, in the portion of the polypeptide outside the domain(s) forming intermolecular contacts). In preferred embodiments, a conservative amino acid substitution typically does not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in PROTEINS, STRUCTURES AND MOLECULAR PRINCIPLES, (Creighton, Ed.), 1984, W. H. Freeman and Company, New York; INTRODUCTION TO PROTEIN STRUCTURE (C. Branden and J. Tooze, eds.), 1991, Garland Publishing, New York, N.Y.; and Thornton et al., 1991, Nature 354:105, each of which are incorporated herein by reference.

Peptide analogs are commonly used in the pharmaceutical industry as non-peptide drugs with properties analogous to those of the template peptide. These types of non-peptide compound are termed "peptide mimetics" or "peptidomimetics". See Fauchere, 1986, Adv. Drug Res. 15:29; Veber & Freidinger, 1985, TINS p. 392; and Evans et al., 1987, J. Med. Chem. 30:1229, which are incorporated herein by reference for any purpose. Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —CH2-NH—, —CH2-S—, —CH2-CH2-, —CH=CH—(cis and trans), —COCH2-, —CH(OH)CH2-, and —CH2SO—, by methods well known in the art. Systematic substitution of one or more amino acids of a consensus sequence with a d-amino acid of the same type (e.g., d-lysine in place of l-lysine) may be used in certain embodiments to generate more stable peptides. In addition, constrained peptides comprising a consensus sequence or a substantially identical consensus sequence variation may be generated by methods known in the art (Rizo & Gierasch, 1992, Ann. Rev. Biochem. 61:387, incorporated herein by reference for any purpose); for example, by adding internal cysteine residues capable of forming intramolecular disulfide bridges which cyclize the peptide.

Characteristics of IL-9 Mutein Receptor Antagonists

As used herein, "wild-type IL-9" or "wt IL-9" means the post-translationally modified human Interleukin-9 polypeptide, whether native or recombinant, having the normally occurring amino-acid sequence of native human IL-9 as disclosed in U.S. Pat. No. 5,734,034. Wild-type IL-9 translated from its corresponding mRNA is 144 amino acids in length (SEQ ID NO. 15), which includes a signal sequence of the N-terminal 18 amino acids. Eukaryotic cells post-translationally modify wild-type IL-9 to make "mature" wild-type IL-9, amino acid residues 19 through 144.

As used herein, "IL-9 mutein" means a mature IL-9 polypeptide comprised of specific amino acid substitutions in the mature human interleukin-9 protein made at positions designated in accordance with wild-type human IL-9. Preferred mutations are in the D helix of wt IL-9 identified as amino acid residues 119 to 138. More preferable are substitutions to those amino acids that produce antagonists of wild type IL-9. Still more preferable are substitutions at positions 126, 133, 134 and 136. Most preferred embodiments of this invention include single mutations in the wt IL-9 peptide wherein the substitution made is at position 133 is Gln to Lys (SEQ ID NO. 21), the substitution at 136 is Lys to Asp (SEQ ID NO. 17), the substitution at position 134 is Lys to Glu (SEQ ID NO. 19), or an IL-9 mutein wherein two substitutions are made: Lys to Glu at position 126 and Gln to Lys at position 133 (SEQ ID NOS. 24). Said engineered substitutions from the wild-type IL-9 protein create unique IL-9 muteins that function as antagonists of wild-type IL-9. Each IL-9 mutein is post-translationally modified by eukaryotic cells producing the mature IL-9 mutein, amino acid residues 19 through 144.

Wild-type IL-9 and IL-9 muteins, as used herein, also include multimers of wild-type IL-9 molecules or IL-9 muteins that are translated as one polypeptide, as well as fragments thereof, which are capable of having either wild-type IL-9 activity or inhibiting wild-type IL-9 activity (SEQ ID NOS. 16, 18, 20, 22, 23, 25, 28 and 29). A dimer IL-9 mutein, for example, is translated as amino acid residues 1 through 144 with the C-terminus of the polypeptide covalently linked to the N-terminus of the proceeding IL-9 mutein not containing the signal sequence, amino acids residues 19 through 144. The resulting polypeptide is 270 amino acids in length and is post-translationally modified to be a mature IL-9 mutein dimer, amino acid residues 19 through 270. Furthermore, an amino acid substitution of a cysteine to a serine at position 147 exists in dimer molecules. Also included is a dimer mutein consisting of a N-terminal polyhistidine purification tag and a proteolytic enzyme cleavage site such as from the Tobacco Etch Virus (TEV) site (SEQ ID NO. 28) as encoded by the polynucleotide represented by SEQ ID NO. 14. Enzymatic cleavage with TEV protease of the polypeptide depicted in SEQ ID NO. 28 as outlined below yields SEQ ID NO. 29, also an object of this invention.

The IL-9 mutein as used herein also includes fusion proteins in which an IL-9 mutein is translated to include an Fc region of an immunoglobulin molecule at either the N-terminus or the C-terminus of the IL-9 mutein, as well as fragments thereof, whereby they are capable of antagonizing wild-type IL-9 activity (SEQ ID NOS. 26 and 27).

Polynucleotides Encoding IL-9 Antagonist Muteins

The present invention also provides polynucleotides encoding IL-9 muteins of this invention, as well as attendant vectors necessary to recombinantly express the polypeptides of this invention. These polynucleotides, vectors and host cells can be used, for example, to produce quantities of the antagonists for therapeutic use. Alternatively, these polypeptides can be used with viral delivery systems to infect host cells, which would allow such cells to produce IL-9 muteins as a therapeutic agent or as an agent to antagonize wild-type IL-9 activity. Polynucleotides that can be used to produce IL-9 muteins of the present invention are shown in FIG. 1 (SEQ ID NOS.: 3-14).

IL-9 cDNA of the present invention was amplified from phytohemaglutinin-activated peripheral blood lymphocyte cDNA to introduce a Bgl II site at the 5' end and an Xba I site at the 3' end of the complete IL-9 cDNA. A C-terminal HistidineX6 tag was added to the wild-type cDNA by PCR mutagenesis. This product was cloned into M13mp19 to allow mutagenesis by a known method.

High Throughput Generation of IL-9 Muteins

Two generalized methods were use to produce mutations in IL-9 at predetermined positions within the protein. In one method, IL-9 muteins were generated by PCR-based techniques when the desired changes in amino acid composition were less than 25 amino acids from either the N- or C-terminus of the protein. IL-9 or IL-9 mutein DNA as template DNA and mutagenic oligomers were used to amplify the IL-9 gene containing the new sequence(s). The PCR fragments were gel purified and cloned into a Bayer plasmid. QuickChange® (Stratagene) mutagenesis using standard protocols was performed on plasmid DNA containing the IL-9 gene when PCR-based mutagenesis was not convenient. The plasmid DNA was transformed into E. coli, the plasmid was amplified, purified, and the gene sequenced. Verified DNA sequences were then used for protein expression.

In the second method, hIL-9 dimer muteins and Fc constructs were made by introducing unique restriction enzyme sites into the hIL-9 mutein at the 3' and/or 5' ends of the gene by PCR based methods. The PCR fragments were restricted and cloned into the expression vector that has been restricted previously with the same restriction enzyme(s). The H6TEV K126E/Q133K dimer polynucleotide (SEQ ID No. 14) was constructed from an expression plasmid containing K126E/Q133K Dimer polynucleotide (SEQ ID No. 1) and two purified DNA oligos using the QuickChange method. Q133K Trimer polynucleotide (SEQ ID No. 9) was obtained from a Q133K Dimer polynucleotide (SEQ ID No. 8) QuickChange experiment.

Protein Expression

Rapidly dividing HKB11 cells (ATCC CRL-12569) were transfected with plasmid DNA containing an IL-9 mutein polynucleotide. The DNA was transfected into the cells using at least 0.2 µg DNA per million cells complexed with Lipofectamine transfection reagent (Gibco BRL) and a transfection agent such as any commercially available reagent for this purpose. Cells were grown at 37° C. for 2 to 10 days. The cell density was maintained at approximately one million cells per milliliter by expanding the culture every two to three days. Cells were separated from the supernatant by centrifugation and the supernatant was purified immediately or supplemented with a cryoprotective reagent such as 10% glycerol or 10% ethylene glycol and stored at −20° C. or below.

Concentration and Exchange of Cell Supernatants

Either of two methods was used to remove small molecule contaminants from the supernatants containing either a wild-type IL-9 protein or an IL-9 mutein protein. For small-scale expression, HKB11 supernatant was concentrated using a spin column with a molecular cut-off of 30,000 kilodaltons or less. The concentrated supernatant was diluted 20-fold into a low salt buffer with a pH 6.5-9.0 and concentrated using the same spin column. A second dilution was performed and the supernatant was concentrated a third time to achieve about a 400-fold buffer exchange of the supernatant into a buffer such as PBS supplemented with 10% glycerol.

Alternatively, and for volumes of HKB11 cells supernatant greater than 100 ml, a column packed with immobilized heparin at a density of about 10 mg/ml or a highly charged ionic resin such as Bakerbond Carboxy-Sulfon was used to capture IL-9 proteins and IL-9 mutein proteins from HKB11 supernatant. The column was equilibrated in phosphate buffered saline at pH 7.2 and an ionic strength equivalent to approximately 130 mM NaCl. Cell culture supernatant was then perfused through the column. The volumetric binding capacity of the column will vary with feed total protein concentration, and will have to be determined empirically by methods known to those skilled in the art. After loading, the column was washed with several column volumes of PBS or other equilibration buffer to remove small molecule contaminants, as well as DNA and lipids. The column was then eluted with PBS containing an additional 500 mM NaCl. The eluate was to be further processed by affinity purification for polyhistidine tagged proteins.

IMAC Purification of H6TEV Constructs

A chelating resin, such as Pharmacia Chelating Sepharose, charged with a metal ion such as nickel, was equilibrated in PBS (pH 7.0) supplemented to 500 mM NaCl to prevent non-specific binding of the tagged-protein. Prepared HKB11 supernatant by concentration and exchange was applied to the IMAC column, followed by several column volumes of equilibration buffer wash. Non-tagged protein impurities typically bind to the resin, and were washed away with equilibration buffer adjusted to 10-20 mM imidazole. The IMAC column is then eluted with PBS adjusted to 250 mM imidazole, pH 7.5. Different tagged constructs exhibit varying strengths of IMAC binding, and in some cases imidazole concentrations greater or less than 250 mM may be required for efficient elution. The polyhistidine-tagged protein is greater than 80% pure; however, additional purification procedures are required to obtain pure protein without a polyhistidine tag. Ideally, the polyhistidine tag should be removed from the protein by a highly specific protease such as a polyhistidine-tagged TEV protease. After TEV proteolysis at 4 degrees Celsius, the protein solution should be exchanged into a buffer free of histidine, EDTA, or DTT such as PBS or PBS supplemented with NaCl, and purified to homogeneity by flowing the protease cleaved protein over a prepared IMAC column. Only the tag-free protein passes directly through the IMAC column and is collected in the flow-through.

Purification Of Fc-Tagged Proteins

An immobilized protein-A or protein-G support, such as Protein-A HyperD, was equilibrated in PBS or similar buffer. Cell culture supernatant was then perfused through the column. The volumetric binding capacity of the Protein-A/G column will vary with feed target protein concentration, and was determined empirically in each case. After loading, impurities were removed by washing with several column volumes of equilibration buffer. The column was further purified with sub-eluting concentrations of MgCl2 below 3M. Wash and elution buffers containing MgCl2 were prepared by titrating the solution pH up to neutrality with ethanolamine. After column washing, the Fc-tagged protein was eluted with 4M MgCl2.

Alternatively, MEP-Hypercell resin from BioSepra was equilibrated in PBS or a similar buffer. Concentrated heparin-column eluate was then applied. After loading, the column was washed with several column volumes of equilibration buffer to remove impurities. Washes with sub-eluting ethylene glycol concentrations less than 50% provided additional impurity clearance. The MEP-Hypercell column is then eluted with PBS adjusted to 50% weight/volume ethylene glycol.

Quantification of Wild-Type IL-9 and IL-9 Muteins and their Storage

Protein concentrations were routinely determined by quantitative Western blot analysis. A control IL-9 sample with known concentration was run on each gel to determine the concentrations of wild-type IL-9 or IL-9 muteins in unknown samples. Purified wild-type IL-9 muteins were stored in a neutral buffer such as PBS plus 10% glycerol and stored at less than −20° C. until needed.

Assessment of Therapeutic Utility of Human Antagonists

To assess the efficacy of a particular antagonist in allergic asthma therapy, the antagonist was tested in vitro in Mo7E proliferation assays as detailed in Example 1 or in eosinophil survival assays as detailed in Example 2. The potency of agonists is expressed herein in terms of an 'EC50' value where EC50 is defined as the concentration of an agent at which 50% of maximal activity is achieved. The potency of antagonists is expressed herein in terms of an 'IC50' value wherein IC50 is defined as the concentration of an agent at which 50% of maximal inhibition of wild type IL-9 activity is achieved.

Pharmaceutical Compositions

Any of the IL-9 antagonist muteins described above can be provided in a pharmaceutical composition comprising a pharmaceutically acceptable carrier. The pharmaceutically acceptable carrier preferably is non-pyrogenic. The compositions can be administered alone or in combination with at least one other agent, such as a stabilizing compound, which can be administered in any sterile, biocompatible pharmaceutical carrier, including, but not limited to, saline, buffered saline, dextrose, and water. A variety of aqueous carriers may be employed, e.g., 0.4% saline, 0.3% glycine, and the like. These solutions are sterile and generally free of particulate matter. These solutions may be sterilized by conventional, well-known sterilization techniques (e.g., filtration). The compositions may contain pharmaceutically acceptable auxiliary substances as required to approximate physiological conditions such as pH adjusting and buffering agents, etc. The concentration of the IL-9 mutein of the invention in such pharmaceutical formulation can vary widely, i.e., from less than about 0.5% or to as much as 20% by weight and will be selected primarily based on fluid volumes, viscosities, etc., according to the particular mode of administration selected. If desired, more than one type of antagonist, for example with a different IC50 for IL-9 antagonism, can be included in a pharmaceutical composition.

The compositions can be administered to a patient alone, or in combination with other agents, drugs or hormones. In addition to the active ingredients, these pharmaceutical compositions can contain suitable pharmaceutically acceptable carriers comprising excipients and auxiliaries that facilitate processing of the active compounds into preparations which can be used pharmaceutically. Pharmaceutical compositions of the invention can be administered by any number of routes including, but not limited to intravenous, intramuscular, intra-arterial, intrathecal, intraventricular, transdermal, subcutaneous, intraperitoneal, intranasal, parenteral, or rectal means.

After pharmaceutical compositions have been prepared, they can be placed in an appropriate container and labeled for treatment of an indicated condition. Such labeling would include amount, frequency, and method of administration.

Therapeutic Methods

The present invention provides IL-9 muteins that can ameliorate symptoms of any disorder caused by IL-9-mediated activity. These disorders include, without limitation, allergy, asthma, chronic obstructive pulmonary disease (emphysema and chronic bronchitis), pulmonary and gastro-intestinal mucus hyperplasia, inflammation, immunological disorders, cancer, leukemia, and lymphoma. The present invention also provides multimers of wild-type IL-9 and Fc-fusion constructs of wild-type IL-9 that may be beneficial to individuals suffering from silicosis or fibrosis or other conditions whereby augmenting the immune system with wild-type IL-9 might be beneficial.

In one embodiment of the invention, a therapeutically effective dose of an IL-9 mutein of the invention is administered to a patient having a disorder characterized by elevated IL-9 activity or in which IL-9 is a critical autocrine growth factor such as those disorders above.

Determination of a Therapeutically Effective Dose

The determination of a therapeutically effective dose is well within the capability of those skilled in the art. A therapeutically effective dose refers to the amount of antagonist that is used to effectively treat a relevant disease compared with the efficacy that is evident in the absence of the therapeutically effective dose.

The therapeutically effective dose can be estimated initially in animal models such as cynomolgus monkeys. The animal model also can be used to determine the appropriate concentration range and route of administration. Such information can then be used to determine useful doses and routes for administration in humans.

Therapeutic efficacy and toxicity, e.g., ED50 (the dose therapeutically effective in 50% of the population) and LD50 (the dose lethal to 50% of the population) of a human antagonist, can be determined by standard pharmaceutical procedures in experimental animals. The dose ratio of toxic to therapeutic effects is the therapeutic index, and it can be expressed as the ratio, LD50/ED50.

Pharmaceutical compositions that exhibit large therapeutic indices are preferred. The data obtained from animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner based upon factors related to the patient who requires treatment. Dosage and administration are adjusted to provide sufficient levels of the antagonist or to maintain the desired effect. Factors that can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

The mode of administration of IL-9 mutein containing pharmaceutical compositions of the invention can be any suitable route which delivers the antagonist to the host. Pharmaceutical compositions of the invention are particularly useful for parenteral administration, i.e., subcutaneous, intramuscular, intravenous, or intranasal administration.

The above disclosure generally describes the present invention. A more complete understanding can be obtained by reference to the following specific examples, which are provided for purposes of illustration only and are not intended to limit the scope of the invention.

EXAMPLE 1

Mo7e Proliferation Assay

The Mo7e cell line was obtained from the Deutsche Sammlung von Mikroorganismen und Zellkulturen GmbH (Braunschweig, Germany) and maintained in RPMI-1640 with 10% fetal calf serum (RPMI-10), 10 ng/ml GM-CSF and penicillin. The Mo7e cell line was established from the peripheral blood of a 6-month old girl with a megakaryoblastic leukemia (AML M7) at diagnosis in 1987. All cell culture reagents were obtained from Invitrogen (Carlsbad, Calif.) unless otherwise noted. Prior to experiments, Mo7e cells were starved of GM-CSF overnight and plated at 10E4 cells/well in RPMI-10 cell culture media at a total volume of 100 μl/well. Cells were treated with IL-9 mutein or wild-type IL-9 for three to four days. For antagonism experiments, cells were treated with 0.357 nM wild-type IL-9 and various concentrations of an IL-9 mutein necessary to generate a dose-response curve. In the final 24 hours of treatment, either 10 μl of AlamarBlue (BioSource, Camarillo, Calif.) or 1 μCi of 3H-thymidine (Amersham) was added to each well. Metabolic reduction of the AlamarBlue was determined by measurement of fluorescence at 530/590 nm using a WALLAC Victor 2 plate reader (Turku, Finland). Incorporation of 3H-thymidine was measured by harvesting the cells onto a 96-well format filtermat (Tomtec harvester, Hamden, Conn.) and reading counts per minute on a WALLAC 1205 BetaPlate reader (Turku, Finland). All cell proliferation data were normalized to controls. The EC50 was determined by the proliferative activity of each wild-type IL-9 protein plotted as a function of concentration. The IC50 was determined by the ability of each IL-9 mutein to inhibit the proliferative activity of Mo7e cells treated with 0.357 nM wild-type IL-9 plotted as a function of IL-9 mutein concentration. The data were analyzed by nonlinear regression using GraphPad Prism software to determine the EC50 or IC50 for each polypeptide.

The potency of the dimerized wild-type IL-9 was the same as that of the wild type IL-9 monomer (FIG. 3). Monomer mutein constructs demonstrated significant antagonism of IL-9 mediated MO7e proliferation with IC50 values ranging from 4.16 nM to 403.80 nM (FIG. 4). The dimer mutein construct K126E/Q133K also demonstrated significant antagonist activity with an IC50 of 3.51. Amino- and carboxy-terminal Fc-fusion constructs of the K126E/Q133K mutein exhibited IC50's of 1.15 and 0.66 nM, respectively. These data demonstrate that IL-9-mediated effects in Mo7E cells can be antagonized by IL-9 muteins and that said muteins have therapeutic value in treating diseases promoted by IL-9 agonism.

EXAMPLE 2

Eosinophil Survival Assay

Human primary eosinophils were freshly isolated from peripheral blood using a magnetic bead anti-CD16 negative selection protocol published by the bead manufacturer (Miltenyi Biotec, Auburn, Calif.). Briefly, EDTA-buffered whole blood was separated on a Ficoll® gradient. The erythrocyte/granulocyte pellet was reserved and resuspended in RPMI-1640. The erythocytes were then precipitated by the addition of ⅓ volume of 4.5% dextran sulfate. The granulocyte layer was reserved and residual erythrocytes were lysed with 0.2× phosphate buffered saline for 1 min. Addition of 1.8× phosphate buffered saline neutralized the lysis and the granulocytes were pelleted by centrifugation and reserved. Cells were incubated on ice for 30 min with anti-CD16 beads and separated using a magnetic column. Using this protocol, polymorphonuclear neutrophils bound to the column whereas eosinophils freely flowed through the column and into a collection tube.

Eosinophils were plated in supplemented DMEM with 10% fetal calf serum with varying concentrations of IL-9 mutein or wild-type IL-9 for 3 days for agonism experiments. For antagonism experiments, cells were treated with 7.14 nM wild-type IL-9 and various concentrations of an IL-9 mutein necessary to generate a dose-response curve. Survival was determined by Trypan blue exclusion. The activity of each polypeptide was plotted as a function of concentration and analyzed by nonlinear regression using GraphPad Prism software to determine either the EC50 or the IC50 for each polypeptide tested. All cell survival data were normalized to controls for each experiment and presented in Table 5 as an IC50 for antagonist activity for each mutein. Non FC-fusion monomer constructs assayed showed significant antagonism of IL-9-mediated eosinophil survival with IC50 values ranging from 32.50 nM to 121.70 nM while corresponding mutein multimers' IC50 values were between 2.85 nM and 177.44 nM. Amino and carboxy-terminal Fc-fusion constructs of the K126E/Q133K mutein exhibited IC50s of 25.48 and 4.92 nM, respectively. These data demonstrate that IL-9-mediated effects in eosinophils can be antagonized by IL-9 muteins and that said muteins have therapeutic value in treating diseases promoted by IL-9 agonism.

We claim:

1. An isolated and purified IL-9 mutein numbered in accordance with wild type IL-9 wherein said mutein is an IL-9 antagonist and comprises at least one amino-acid substitution, wherein said amino acid substitution is in the D helix at a position selected from the group consisting of 119-138.

2. The isolated and purified IL-9 mutein of claim 1 wherein said substitution is at a position selected from the group of consisting of 126, 133, 134 and 136.

3. The isolated and purified IL-9 mutein of claim 2 wherein said substitution at position 133 is Gln to Lys (SEQ ID NO. 21).

4. The isolated and purified IL-9 mutein of claim 2 wherein said substitution at position 134 is Lys to Glu (SEQ ID NO. 19).

5. The isolated and purified IL-9 mutein of claim 2 wherein said substitution at position 136 is Lys to Asp (SEQ ID NO. 17).

6. The IL-9 mutein of claim 1, wherein said mutein inhibits the proliferative response of Mo7E cells to IL-9 with an IC50 value of about 0.1 nM to about 10 μM.

7. The IL-9 mutein of claim 1, wherein said mutein inhibits the proliferative response of Mo7E cells to IL-9 with an IC50 value of about 0.5 nM to about 1 μM.

8. The IL-9 mutein of claim 1, wherein said mutein inhibits the proliferative response of Mo7E cells to IL-9 with an IC50 value of about 1.0 nM to about 100 nM.

9. The IL-9 mutein of claim 1, wherein said mutein inhibits the anti-apoptotic response of eosinophils to IL-9 with an IC50 value of about 0.1 nM to about 10 μM.

10. The IL-9 mutein of claim 1, wherein said mutein inhibits the anti-apoptotic response of eosinophils to IL-9 with an IC50 value of about 0.5 nM to about 1 μM.

11. The IL-9 mutein of claim 1, wherein said mutein inhibits the anti-apoptotic response of eosinophils to IL-9 with an IC50 value of about 1.0 nM to about 100 nM.

12. An isolated and purified IL-9 mutein numbered in accordance with wild type IL-9 wherein said mutein is an IL-9 antagonist and comprises at least one amino-acid substitution, wherein said substitution at position 126 is Lys to Glu and at 133 is Gln to Lys (SEQ ID NO. 24).

* * * * *